United States Patent [19]

Klee et al.

[11] Patent Number: 5,589,583
[45] Date of Patent: Dec. 31, 1996

[54] PLANT PROMOTER

[75] Inventors: Harry J. Klee, Ballwin; James S. Elmer, Ellisville, both of Mo.

[73] Assignee: Monsanto Company, St. Louis, Mo.

[21] Appl. No.: 463,682

[22] Filed: Jan. 11, 1990

[51] Int. Cl.$^6$ .......................... C12N 15/82; C12N 15/11; C12N 15/67; A01H 5/00

[52] U.S. Cl. .................... 536/24.1; 435/69.1; 435/240.4; 435/320.1; 800/205; 800/250; 935/35

[58] Field of Search .............................. 435/69.1, 320.1, 435/240.4; 536/27, 24.1; 800/205, 250; 935/35

[56] References Cited

U.S. PATENT DOCUMENTS 4,962,028  10/1990  Bedbrook et al. ................. 435/172.3

OTHER PUBLICATIONS

Medford et al 1991 The Plant Cell 3: 359–370.
Teeri et al 1986 The EMBO J 5: 1755–1760.
Schell. 1987 Science 237: 1176–1183.
Pokalsky et al 1989 (Jun.) Nucleic Acid Res 17: 4661–4673.
Knox et al 1989 (May) Development 106: 47–56.
Schmulling et al 1989 (Jul.) The Plant Cell 1:665–670.
Kolosha et al 1986 FEBS Letters 197: 89–92.

Primary Examiner—Patricia R. Moody
Attorney, Agent, or Firm—Thomas P. McBride; Dennis R. Hoerner, Jr.

[57] ABSTRACT

A plant promoter that is a nucleic acid region located upstream of the 5' end of a plant DNA structural coding sequence that is transcribed at high levels in meristematic tissue and/or rapidly dividing cells. This promoter region is capable of conferring high levels of transcription in meristematic tissue and/or rapidly dividing cells when used as a promoter for a heterologous coding sequence in a chimetic gene. The promoter and any chimeric gene in which it may be used can be used to obtain transformed plants or plant cells. A DNA coding sequence that codes for a gene that is highly transcribed in meristematic tissue of *Arabidopsis thaliana* is also disclosed. This coding sequence can be used to obtain a cDNA probe useful in obtaining analogous promoters from a homologous coding sequence in other plant species. Chimeric genes including the isolated promoter region, transformed plants containing the isolated promoter region, transformed plant cells and seeds are also disclosed.

17 Claims, 9 Drawing Sheets

```
gaattcaaaagagctaaacaacatatttctaacaaataatatgctcatgcatgctaatat
ttactgtaacatttaaaaaaattaaggatggtaaacataatctgcttaccaaatgatgga
gatactcaagagtccagctgtaatacatcttgcatgcaatatcttgatattagcctcctt
ttgttcacccactctcttctcttcttctcatttatttatatgttaaactctctccca
ctatatatatctctccccttcttctctcttcctCACATTCCTCACCAAACCCTCTCCAA
AACACACCCACACGTACGCACACACACAAAGACAATGTCTCCTTTCAAAATATTCTTCTT
                                   M  S  P  F  K  I  F  F  F
CACGACTCTTCTCGTGGCGGCGTTTTCAGTGTCGGCTGCTGATTTCAACACTGACGTCAA
  T  T  L  L  V  A  A  F  S  V  S  A  A  D  F  N  T  D  V  N
CGTAGCTTGGGGAAATGGCCGTGGGAAGATACTCAACAACGGCCAGCTTCTTACTCTCTC
  V  A  W  G  N  G  R  G  K  I  L  N  N  G  Q  L  L  T  L  S
CTTAGACAAATCCTCTGGTTCCGGTTTTCAATCCAAAACAGAGTATTTGTTTGGAAAGAT
  L  D  K  S  S  G  S  G  F  Q  S  K  T  E  Y  L  F  G  K  I
TGATATGCAGATTAAGCTTGTTCCTGGTAACTCTGCAGGAACAGTCACAACTTTTTACGT
  D  M  Q  I  K  L  V  P  G  N  S  A  G  T  V  T  T  F  Y
GAGTTTATATATTTTCTTTAGGAGTTTTAAGTGATTTTGGATTTGGTTTTTATATTGAGA
CTTCATCTTGACATTTTTGTGTATTTGCAGCTAAAATCCGAAGGATCCACTTGGGATGAG
                                    L  K  S  E  G  S  T  W  D  E
ATTGATTTTGAGTTCTTGGGTAATATGAGTGGAGATCCTTATACTTTACACACTAATGTT
  I  D  F  E  F  L  G  N  M  S  G  D  P  Y  T  L  H  T  N  V
TACACTCAAGGTAAAGGTGACAAAGAGCAACAATTCCATCTCTGGTTCGACCCAACCGCC
  Y  T  Q  G  K  G  D  K  E  Q  Q  F  H  L  W  F  D  P  T  A
AATTTCCACACTTACTCAATCCTCTGGAACCCTCAAAGAATCATGTAAAGACAACAATCT
  N  F  H  T  Y  S  I  L  W  N  P  Q  R  I  I
CACCTTTCTTGCTACACACGTTAATAAACCCTAACTAGGTTTCGATTTTCTTACCCATCT
CTTATCTGTTCTGTTTTCTATCAGATTGACCGTCGATACACACCCATTAGAGAGTTTAAA
                       L  T  V  D  T  H  P  L  E  S  L  K
AACTATGAGTCTCTCGGTGTCTTGTTTCCAAAGAACGAAGCCGATGAGGATGGTACGGCA
  T  M  S  L  S  V  S  C  F  Q  R  T  K  P  M  R  M  V  R  Q
GTTTATGGAACGGCAGAGCGATTGGGCAACGAAGAGGCGGTCTTGGTTAAAACTGATTGG
  F  M  E  R  Q  S  D  W  A  T  K  R  R  S  W  L  K  L  I  G
TCTAAAGCTCCATTCATGGCTTCTTACAGAAACATTAAGATTGACTCGAAACCAAACTCC
  L  K  L  H  S  W  L  L  T  E  T  L  R  L  T  R  N  Q  T  P
AATTGGTACACTCAAGAAATGGATTCAACAAGCCAAGCTAGACTCAAATGGGTTCAGAAG
  I  G  T  L  K  K  W  I  Q  Q  A  K  L  D  S  N  G  F  R  R
AATTACATGATCTACAATTATTGTACTGACCATAGGAGGTTTCCACAGGGAGCTCCTAAG
  I  T  *
GAATGCACAACAAGCTCATAGAATCTCAAATTATATTCTATTTATTTATCTACGCTTCCT
CTCTTTCTTTTATGTGAAAATTGTGAATGCTCTGTTTATAGCTTGTCTATTATGTCCGAG
AATTTCTTTTTCTGTTTTTGATTCTTTTCGTTGTATATCTTTGTCCAATAAAGGAAATGA
TGTGTCTTTACTCTTATAGATATGTATAAAAGATGTCCCTGTTTTATTTGTTAAAAAAA
ATTGTTTATGATAATGATAGTTCTTTCTTCTTC
```

Fig. 1

S = SalI
E = EcoRI
B = BamHI 5,589,583

PLANT PROMOTER

This invention relates in general to promoters for use in plant genetic engineering and more particularly to a promoter that is capable of conferring high levels of transcription of chimeric genes in meristematic tissue and/or rapidly dividing cells.

One of the goals of plant genetic engineering is to obtain plants having improved characteristics or traits. Many different types of characteristics or traits are considered advantageous, but those of particular importance include resistance to plant diseases, resistance to insects, resistance to herbicides, enhanced stability or shelf-life of the ultimate consumer product obtained from the plant or improvements in the nutritional value of the edible portions of the plant. Recent advances in genetic engineering have enabled researchers in the field to obtain plants expressing or containing a desired quality. This permits a desired gene (or genes) from a source different than the plant of interest or a gene native to the desired plant, but engineered to have different or improved qualities, to be incorporated into the plant's genome. This new gene (or genes) can then be expressed in the plant cell to exhibit the new trait or characteristic.

In order for the newly inserted gene to express the protein for which it codes in the plant cell, the proper regulatory signals must be present and in the proper location with respect to the gene. These regulatory signals include a promoter region, a 5' non-translated leader sequence and a 3' polyadenylation sequence.

A promoter is a DNA sequence that directs the cellular machinery of a plant to produce RNA from the contiguous structural coding sequence downstream (3') to the promoter. The promoter region influences the rate at which the RNA product of the gene and resultant protein product of the gene is made, The 3' polyadenylation signal is a non-translated region that functions in the plant cells to cause the addition of polyadenylate nucleotides to the 3' end of the RNA to enable the mRNA to be transported to the cytoplasm and to stabilize the mRNA for subsequent translation of the RNA to produce protein.

It has been shown that certain promoters are able to direct RNA synthesis at a higher rate than others. These are called "strong promoters". Certain other promoters have been shown to direct RNA production at higher levels only in particular types of cells or tissues and are often referred to as "tissue-specific promoters". Promoters that are capable of directing RNA production in many or all tissues of a plant are called "constitutive promoters". Therefore, expression of a chimeric gene (or genes) introduced into a plant may potentially be controlled by identifying and using a promoter with the desired characteristics.

Several promoters capable of regulating the translation of a gene introduced into a plant cell are known. The most widely used promoter is the 35S promoter from the cauliflower mosaic virus (CaMV35S promoter). This promoter is a strong, constitutive promoter that causes expression in virtually all cells and tissues of the transformed plant. Other constitutive promoters that are known include the promoter from the mannopine synthase gene and the nopaline synthase gene of the T-DNA of *Agrobacterium tumefaciens*. If a promoter region were identified that conferred high levels of transcription in meristematic tissue and/or rapidly dividing cells, it would not be known whether that promoter region would continue to operate in a similar manner if excised from its native coding sequence and utilized in a chimeric gene. It would be desirable to obtain a promoter that confers high levels of expression in these rapidly growing cells and meristematic tissues and that maintains this tissue specificity and expression characteristics when isolated and utilized as the promoter for a heterologous coding sequence in a chimetic gene.

It is therefore a primary object of the present invention to provide a plant promoter region that is capable of conferring high levels of transcription in rapidly dividing cells of transformed plants when coupled with a heterologous coding sequence in a chimeric gene.

It is another object of the present invention to provide such a promoter region that is also capable of conferring high levels of transcription in meristematic tissue of transformed plants when coupled with a heterologous coding sequence in a chimeric gene.

It is a further object of the present invention to provide such a promoter region from *Arabidopsis thaliana* that is capable of transcribing a heterologous gene at high levels in meristematic regions of a transformed plant.

It is yet another object of the present invention to provide a cDNA probe that corresponds to the DNA coding sequence of an *Arabidopsis thaliana* coding sequence that is highly expressed in meristematic tissue for screening genomic libraries of other plant species for a coding sequence that is capable of hybridizing to the cDNA probe to identify a coding sequence essentially homologous to the *A. thaliana* coding sequence in order to obtain promoter regions from other plant species that are capable of conferring high levels of expression in meristematic tissue and/or rapidly dividing cells.

It is a still further object of the present invention to provide a plant promoter comprising a region of DNA located at the 5' end of a plant DNA structural coding sequence that is homologous to a DNA coding sequence from *A. thaliana* that is found to confer high levels of transcription in meristematic tissue.

These and further objects of this invention will be made clear or become apparent from the following description and claims when read in light of the accompanying drawings.

SUMMARY OF THE INVENTION

The present invention provides a plant promoter that comprises a nucleic acid region located upstream of the 5' end of a plant DNA structural coding sequence that is transcribed at high levels in meristematic tissue and/or rapidly dividing cells. The isolated promoter region of the DNA coding sequence is of sufficient length such that it is capable of initiating and regulating transcription of a DNA sequence to which it is coupled. The promoter region is typically between 500 bp and 4 kb in length and preferably greater than 1 kb in length. An analogous promoter region can be obtained from any plant species that has a DNA structural coding sequence that is highly transcribed in the meristematic tissue and/or rapidly dividing cells of the plant so long as the DNA coding sequence is capable of hybridizing to an *A. thaliana* cDNA probe having essentially the DNA sequence as shown in FIG. 1. The DNA sequence of FIG. 1 is of a coding sequence found in *A. thaliana* that is found to be highly transcribed in meristematic tissue. The sequence is arranged in 5'–3' fashion with a portion of the 5' upstream sequence being illustrated in lower case letters. The beginning of the nucleotides in upper case letters illustrates the beginning of the 5' non-translated leader sequence. In the structural coding sequence, the amino acid that corresponds to the particular codon is shown using the single letter amino acid abbreviation. The abbreviation is placed underneath the first nucleotide of the corresponding codon. The asterisk at the 3' end of the sequence represents the terminator signal. The sequence following the asterisk is 3' downstream non-translated sequence. Introns are also presented. The isolated promoter region is capable of maintaining its ability to confer high levels of transcription in the meristematic tissue when used as a promoter for a heterologous coding sequence in a chimeric gene to be used in transforming plants.

This invention also provides a DNA coding sequence that codes for a sequence that is highly transcribed in the meristematic tissue or rapidly dividing cells in *Arabidopsis thaliana*. The coding sequence can be used to make a probe to isolate homologous coding sequences in other plant species so that the corresponding promoter region from other plant species having the same tissue-specific qualifies can be isolated and used.

A promoter region so isolated can be fused to a desired coding sequence and polyadenylation site to create a chimeric gene. This gene can then be transformed into a plant by any method of choice. In the transformed plant, the promoter will confer high level transcription and expression of the contiguous structural coding sequence in meristematic tissue and/or regions of rapidly dividing cells in the plant.

Hence, in one aspect the present invention provides a plant promoter comprising a region of DNA located at the 5' end of a plant gene that contains a structural DNA coding sequence that is homologous to a DNA sequence as shown in FIG. 1, said region of DNA being capable of conferring high levels of transcription in meristematic tissue or regions of rapidly dividing cells.

A further aspect of the present invention provides a chimeric gene that functions in plant cells which comprises a promoter comprising a region of DNA located at the 5' end of a plant gene that contains a structural DNA coding sequence that is homologous to a DNA sequence as shown in FIG. 1, said region of DNA being capable of conferring high levels of transcription in meristematic tissue or regions of rapidly dividing cells; a structural DNA coding sequence that is heterologous with respect to the promoter; and a 3' non-translated region which encodes a polyadenylation signal which functions in plant cells to cause the addition of polyadenylate nucleotides to the 3' end of the RNA.

In another aspect, the present invention provides a transformed plant cell containing a chimeric gene which comprises a promoter comprising a region of DNA located at the 5' end of a plant gene that contains a structural DNA coding sequence that is homologous to a DNA sequence as shown in FIG. 1, said region of DNA being capable of conferring high levels of transcription in meristematic tissue or regions of rapidly dividing cells; a structural DNA coding sequence that is heterologous with respect to the promoter; and a 3' non-translated region which encodes a polyadenylation signal which functions in plant cells to cause the addition of polyadenylate nucleotides to the 3' end of the RNA.

In yet other aspects, the present invention provides a differentiated plant containing the transformed plant cells described above and seeds of the differentiated plant as well as a method for selectively expressing a chimeric gene in transformed plants or plant cells by using a plant promoter comprising a region of DNA located at the 5' end of a plant gene that contains a structural DNA coding sequence that is homologous to a DNA sequence as shown in FIG. 1, said region of DNA being capable of conferring high levels of transcription in meristematic tissue or regions of rapidly dividing cells.

BRIEF DESCRIPTION OF THE DRAWINGS

FIG. 1 shows the DNA coding sequence of a gene that is found to be highly expressed in meristematic tissue of *Arabidopsis thaliana*.

DETAILED DESCRIPTION OF THE INVENTION

Figure 2:
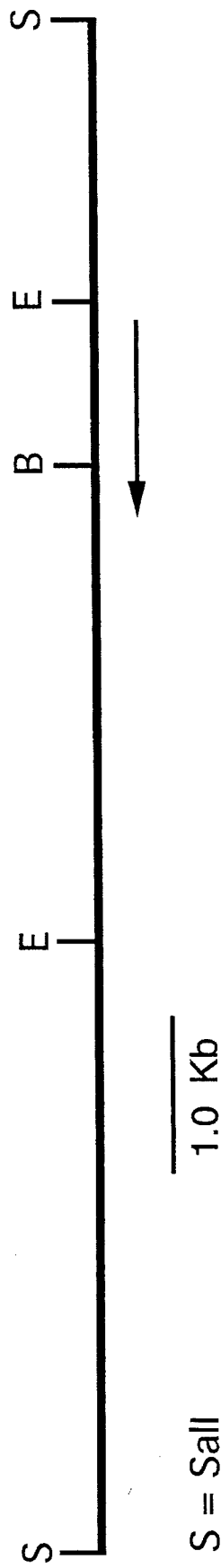
FIG. 2 shows a diagrammatic map of the genomic insert from *Arabidopsis thaliana* in pMON648.

A promoter region of the present invention was discovered by its location adjacent to the start of a DNA structural coding sequence that was found to be transcribed at high levels in meristematic tissue of *Arabidopsis thaliana*. A screening procedure was used to determine if such genes existed as well as to identify low copy number genes which were highly expressed in meristematic regions of a plant. In order to do this, isolation of a sufficient amount of plant tissue enriched for cells that are either meristematic or in a state of rapid growth was necessary. Tissue from cauliflower heads, *Brassica oleraceae*, was chosen for this purpose.

Proliferating cauliflower heads were harvested and the upper 0.5 mm of meristematic tissue shaved with a razor blade. Ribonucleic acid (RNA) was isolated from this tissue using a lithium chloride precipitation procedure as described by Rochester et al. (1986). Polyadenylated mRNA (PolyA+ mRNA) was prepared using oligo dT cellulose chromatography as described by the manufacturer, such as Collaborative Research Co. This RNA was then used to construct a cDNA library using the procedure of Gasser et al. (1989). The RNA was reverse transcribed into first strand cDNA synthesis using oligo dT as a primer. This was followed by second strand cDNA synthesis, DNA methylation and the addition of EcoR1 linkers. Following EcoR1 digestion, the cDNA was selected by only choosing those cDNA of greater than 500 base pairs (bp) in length by agarose gel electrophoresis and column chromatography on an LKB Ultrogel AcA34. The selected cDNA was then ligated into the bacteriophage lambda cloning vector GT10 by the method of Young & Davis (1983). The ligated DNA was packaged in vitro using Stratagene Gigipack Gold and recombinant bactoriophage isolated by growth on *E. coli* C600 hfl+host.

In order to identify CDNA clones that might correspond to highly expressed genes, a cDNA library was plated and plaque lifts were prepared. Replicas of each of the cDNA-containing phage were prepared by growing approximately 5000 individual phage on 15 cm agar-containing plates. The phage were then transferred to nitrocellulose filters where they were lysed and their DNA immobilized using the method as described in Maniatis et al. (1982).

Radiolabelled cDNA was then prepared from cauliflower meristem RNA using reverse transcriptase and oligo-dT primer. Gasser et al. (1989). The radiolabelled cDNA was hybridized to the nitrocellulose filters containing the immobilized cDNA library in 2XSSPE, 2× Denhardt's solution, 0.1% Sodium dodecyl sulfate (SDS), 100 µg/ml denatured salmon sperm DNA and 20 µg/ml polyA for 48 hours at 65° C. Filters were washed in 0.3XSSPE containing 0.1% SDS three times for 15 minutes, twice at room temperature and once at 65° C. and exposed to X-ray film. Under these conditions, the degree of hybridization is directly proportional to the relative abundance of the RNA in the original tissue. The abundance of an RNA is principally a function of the level at which it is transcribed from a corresponding gene or gene family so that strong hybridization indicates a highly expressed RNA. Since abundance of an RNA product is also affected by RNA stability, strong hybridization could also indicate a very stable transcript.

Since many genes are members of complex gene families, the contribution of any single gene of a multimember family to the overall level of expression may be quite low. These genes are not likely to contain strong promoters. Therefore, is was necessary to eliminate from further analysis any phage whose cDNA insert corresponded to highly reiterated genes. To accomplish this, total genomic cauliflower DNA was radiolabelled using the random oligonucleotide procedure. Feinberg et al. (1984). The DNA was then tested for hybridization to a nitrocellulose filter containing duplicate plaque lifts of the cDNA containing phage. The radiolabelled DNA was hybridized to the plaque lifts using the following conditions: 2XSSC (SSC buffer is 1.5M NaCl, 0.3M NaCitrate), 4× Denhardt's solution and 0.1% SDS at 65° C. for 16 hours. Filters were washed three times in 1XSSC, 0.1% SDS at 65° C. for 15 minutes and exposed to X-ray film. Under these conditions, the degree of hybridization of the radiolabelled probe is proportional to the abundance of the gene in the genomic DNA. Thus, the strongest hybridization is obtained to phage clones corresponding to highly reiterated genes which make a darker exposure on the X-ray film. By comparing the intensity of the hybridization signals on the duplicate filters, a low copy number gene which produced an abundant RNA in cauliflower meristems was identified by locating a phage that exhibits strong hybridization to radiolabelled cDNA from cauliflower meristem RNA (observed as a dark exposure on X-ray film), and that is not strongly hybridized to radiolabelled cauliflower genomic DNA (observed as low intensity exposure on X-ray film).

Using the selection criteria described above, approximately 100 cDNA containing phage meeting the selection criteria were chosen as possible-candidates containing a gene having a promoter capable of conferring high level transcription in meristematic tissue. These candidate's were further screened by performing a standard Southern hybridization to digested genomic cauliflower DNA to more accurately determine the copy number of the corresponding genes and to eliminate candidates having less than 300 bp inserts of plant DNA. A cDNA from cauliflower was selected that was determined to have 2-3 copies in the Brassica oleraceae genome. This cDNA was chosen as containing a gene that was highly transcribed in meristematic tissue and that presumably had a promoter region located upstream of its 5' end that was responsible for this tissue-specific transcription.

Once the Brassica oleraceae cDNA was chosen, it was used to screen an Arabidopsis thaliana genomic DNA to identify the existence of a homologous gene and its copy number in the Arabidopsis thaliana genome. The A. thaliana genomic DNA was prepared by standard techniques known to those skilled in the art and the chosen Brassica oleraceae cDNA radiolabelled by an oligolabelling procedure. Feinberg et al. (1984). The A. thaliana genomic DNA was digested with EcoRI, HindIII and BamHI and electrophoresed on a 1% agarose gel containing 1 µg/ml EtBr at 2 V/cm for 3–4 hours. Once the gel had been run, it was immersed in 0.25M HCl solution for 20 minutes, rinsed with distilled water and then immersed in denaturant (0.5N NaOH, 1.5M NaCl) for 1 hour and again rinsed with distilled water. Following this rinse, the gel was immersed in a neutralizer solution (0.5M Tris-Cl, pH 7.0, 3M NaCl) for 1 hour and again rinsed with distilled water. A nylon hybridization membrane was placed atop the gel and this was placed in a container with 10×SSC buffer. Paper towels placed on top of the membrane allowed for movement of the SSC through the gel and concomitant movement of the DNA into the hybridization membrane. This was done for at least 10 hours. Then the membrane was removed from the gel, rinsed in 10×SSC and baked at 80° C. for 2 hours.

The membrane was then incubated in a bag containing 6×SSC, 0.01M EDTA, 5× Denhardt's solution, 100 µg/ml denatured salmon sperm DNA and 0.6% SDS at 45° C. for 2 hours. The radiolabelled Brassica oleraceae cDNA was then boiled for 8 minutes and added to the bag. This was incubated at 45° C. for 24–48 hours.

The membrane was then removed from the bag and immersed in 6×SSC, 0.2% SDS at 45° C. for 30 minutes and then in successively lower concentration of SSC (5×SSC, 4×SSC, 3×SSC etc.) until the background radioactivity. of the membrane was below 0.2 mREM/hour. The membrane was then exposed to X-ray film at −80° C. in complete darkness for 24 hours.

One or two discrete bands were detected in the lanes representing each of the restriction enzyme digests. The small number of hybridizing bands and their weak intensity indicated that the A. thaliana genome contained a single gene homologous to the isolated Brassica oleraceae gene whose corresponding mRNA is found in abundance in meristematic tissue. This single copy gene of A. thaliana was then chosen to identify and isolate its promoter region. Once the gene was chosen, the translational start site of the coding sequence and the promoter-leader/coding sequence junction was determined by the method described herein.

An Arabidopsis thaliana genomic library was then prepared by standard techniques know to those of ordinary skill in the art as herein described. The library was screened for plaques hybridizing to the Brassica oleraceae cDNA in the same manner as also described herein. A plaque containing Arabidopsis thaliana genomic DNA hybridizing to the Brassica cDNA was identified. This plaque was isolated and DNA isolated therefrom.

An 8.0 kb SalI genomic fragment containing the isolated A. thaliana gene was isolated from the plaque DNA and cloned into the SalI site of pUC119 to create pMON648, which is shown in FIG. 2. A 4 kb BamHI fragment from pMON648 containing the presumed A. thaliana promoter region was inserted into the BamHI site of pUC119 to create pMON1575. A BglII site was then introduced into pMON1575 at the junction of the A. thaliana promoter-leader sequence and its corresponding coding sequence by site directed mutagenesis to create pMON1576. The oligonucleotide primer used for this mutagenesis consisted of the following sequence (5'-3'):

GAAAGGAGACAT<u>AGA</u>TCTTTGTGTGTG.

The underlined nucleotides were inserted to create the BglII site. A 2.4 kb BglII-StuI fragment from pMON1576 was further subcloned from this larger fragment. This 2.4 kb fragment contained the entire promoter region of the isolated *A. thaliana* cDNA and was used as a promoter in constructs containing the GUS coding sequence and the EPSPS synthase coding sequence in transformed plants as reporter genes.

An analogous promoter from *Brassica oleraceae* tissue can also be isolated by using a-probe based upon the coding sequence of FIG. 1 hybridized against a *Brassica oleraceae* genomic DNA library. Following identification of the relevant gene and location of the promoter-leader sequence/coding sequence junction, an approximately 2.4 kb promoter region can be excised and tested for functional properties.

A promoter region analogous to the one described above from *A. thaliana* can be isolated from any plant species that has a coding sequence that is capable of hybridizing to a cDNA probe having essentially the coding sequence of FIG. 1 or a fragment of the coding sequence of FIG. 1. It is known that the structural coding sequences of homologous genes often exhibit a high level of sequence conservation. Gasser et al. (1987). It has been further determined that the structural coding sequence of the subject gene of this invention is highly conserved among plant species. Therefore, a cDNA probe of the isolated *A. thaliana* structural coding sequence can be used to identify and isolate analogous promoter regions from other plant species by isolating a homologous gene from a genomic DNA library from meristematic tissue of the subject plant and then identifying the 5' upstream promoter region. The sequence conservation of promoter regions from homologous genes is typically insufficient for this purpose. A homologous gene from another plant species can be identified by hybridization to a cDNA probe of the *A. thaliana* structural coding sequence for the subject gene that is highly expressed in meristematic tissue and/or regions of rapidly dividing cells as shown in FIG. 1. If there are multiple copies of this coding sequence in the species of choice (see step I below), it is possible that not all of the promoters isolated will function in the desired manner. In this case it would be necessary to isolate and screen the promoter for each such coding sequence isolated until one with the desired meristematic function is identified. The following protocol describes how one can isolate an analogous promoter region from any plant species.

I. SOUTHERN HYBRIDIZATION OF GENOMIC DNA FROM A CHOSEN PLANT SPECIES WITH cDNA FROM *A. THALIANA*

The purpose of this step is to determine if a coding sequence from the chosen plant species that is homologous to the *A. thaliana* coding sequence of FIG. 1 can be detected in genomic DNA by differential hybridization to the *A. thaliana* cDNA. If detection is not possible by this method, it will be necessary to identify and isolate a cDNA from the chosen species capable of hybridizing to the *A. thaliana* cDNA of FIG. 1 before a genomic clone can be identified. If detection can be accomplished from genomic DNA, one can skip step II (below) and directly screen a genomic library for a homologous coding sequence using the *A. thaliana* cDNA as the probe. In this case, a second purpose of this step is to provide an estimate of the copy number of the isolated coding sequence in the chosen species.

A. Isolation of genomic DNA
1. Collect about 1 gram (gm) of young leaf tissue.
2. Add 10 milliliters (mls) of extraction buffer and grind with a mortar and pestle until pasty. Extraction buffer comprises:
   50 mM Tris, pH 8.0
   50 mM EDTA
   50 mM NaCl
   400 µg/ml Ethidium Bromide (EtBr)
   2% N-lauryl sarcosine (Sarkosyl)
3. Centrifuge (Cfg) for 30 minutes @12,000 g, 5° C. in a screwcap oakridge tube.
4. Add 0.95 gm CsCl per ml of supernatant.
5. Cfg 20 minutes @10,000 g, 5° C.
6. Remove supernatant and place into centrifuge tubes.
7. Cfg 20–48 hours @44,000 rpm, 20° C., in a Beckman VTi80 rotor or the like.
8. DNA Will appear as an UV fluorescent band in the tube. Extract band from tube using a needle and syringe and place into a clean tube.
9. Add 1 volume of isopropanol (saturated with 20× SSC), mix, let settle, and then remove upper phase which will contain red stain (EtBr). Repeat extraction with saturated isopropanol until all red stain is removed from lower phase.
10. Add 2 volumes of cold ethanol to remaining clear lower phase and cfg@15,000 rpm in a microfuge for 5 minutes.
11. Remove supernatant, let pellet dry and then resuspend in 0.5 ml of TE buffer (10 mM Tris, pH 7.5, 1 mM EDTA).
12. Quantitate the DNA concentration by measuring the UV absorbance of an aliquot at 260 nm wavelength using a spectrophotemeter. One O.D. unit of absorption at this wavelength represents 50 µg of DNA.

This procedure is sufficient for most plant species, but for those species that contain compounds that would hinder this procedure alternate methodologies are available and known in the art.

B. Digestion and electrophoresis of genomic DNA

When the genomic DNA has been isolated, it is then digested separately with EcoRI, HindIII and BamHI restriction enzymes and electrophoresed on an agarose gel according to the following general protocol.
1. Add to a 1.5 ml eppendorf tube:
   10 µg of genomic DNA
   50 µl of 10× enzyme buffer (as suggested by enzyme supplier)
   5 µl of restriction enzyme (New England Biolabs)
   Add distilled water to bring volume to 500 µl.
   Incubate at 37° C. for 4 hours or more.
   The DNA is digested separately with EcoRI, HindIII, and BamHI restriction enzymes.
2. Precipitate DNA by adding 50 µl of 3M Sodium Acetate and 1 ml of ethanol to each tube, chill on dry ice, and cfg@15,000 rpm for 5 minutes. Resuspend pellets in 20 µl of TE buffer.
3. Electrophorese digested genomic DNA (along with Lambda DNA cut with BstelI as a size standard) at 2 V/cm for 3–4 hours through a gel containing:
   1% agarose
   1 µg/ml EtBr
   40 mM Tris-acetate pH 7.5
   1 mM EDTA
   When gel is complete, take a picture of the gel under a UV light using an appropriate camera.

C. Immobilizing DNA onto nylon membrane
1. Immerse the agarose gel in a 0.25M HCl solution for 20 minutes, then rinse gel with distilled water.
2. Immerse gel in denaturant (0.5N NaOH, 1.5M NaCl) for 1 hour, changing the solution once, then rinse with distilled water.

3. Immerse gel in neutralizer (0.5M Tris-Cl, pH 7.0, 3M NaCl) for 1 hour, changing the solution once, then rinse with distilled water.
4. Place gel on Whatman 3MM paper soaking in 10× SSC.
5. Place nylon hybridization membrane (Micron Separations Inc.) soaked in 10× SSC directly onto the surface of the gel. Then place 2 sheets of Whatman 3MM paper on the membrane followed by several sheets of dry paper towels. This will create a movement of 10× SSC through the gel and into the dry towels via capillary action. The DNA in the agarose gel is also moving onto the nylon hybridization membrane. Continue this for at least 10 hours.
6. Remove membrane from gel, rinse in 10× SSC, and bake membrane at 80° C. for 2 hours.

D. Radiolabelling the isolated *A. thaliana* cDNA coding sequence

Labelling of the cDNA with a radioactive deoxynucleotide(s) can be accomplished by an oligolabelling procedure (Feinberg et al., 1983) or by any other preferred method. The oligolabelling procedure described below uses a kit supplied by Pharmacia. The labelled cDNA should be used for hybridization (step E) within a few days after it has been made.

1. Boil 50 ng of purified cDNA in a 1.5 ml tube for 8 minutes, place on ice 1 minute.
2. At 25° C. add to DNA:
   10 µl reagent mix
   2 µl BSA (bovine serum albumin)
   5 µl (50 µCi) P dCTP (3000 Ci/mmole)
   2 µl Klenow Polymerase
   Add distilled water to 50 µl final volume.
   Incubate overnight at room temperature.
   Reagent mix (pH 8.0) contains:
   100 µM dATP
   100 µM dGTP
   100 µM dTTP
   250 mM Tris-HCl (pH 8.0)
   25 mM magnesium chloride
   50 mM 2-mercaptoethanol
   90 O.D. units/ml random hexanucleotide oligomers
3. Add 50 µl of stop solution (contains dCTP, EDTA, SDS, NaCl, and buffer).
4. Purify labelled cDNA from unincorporated P dCTP by passing it through a Sephadex G-50 DNA grade spin column according to the manufacturer's instructions or, alternatively, a Sephadex column can be made in a 5 ml disposable pipette. The labelled cDNA will pass through the column more quickly than the free nucleotide and can thus be separated by collecting the appropriate fraction that elutes from the column. Quantitate the amount of incorporated P dCTP by counting 1 µl of the labelled cDNA using a scintillation counter. The total labelled cDNA should contain at least 100 million cpm (counts per minute) for every 50 ng of DNA used.

E. Hybridizing the isolated *A. thaliana* cDNA coding sequence to immobilized genomic DNA 1. Place nylon hybridization membrane in a bag containing enough hybridization solution for total immersion, seal, and incubate at 45° C. for at least 2 hours.
   Hybridization solution contains:
   6× SSC
   0.01M EDTA
   5× Denhardt's Solution (1 mg/ml of Ficoll, BSA, and polyvinylpyrrolidone)
   100 µg/ml denatured salmon sperm DNA 0.5% SDS
2. Boil the labelled cDNA from step D above for 8 minutes.
3. Add the labelled cDNA to the bag containing the membrane immersed in hybridization solution, reseal. For every milliliter of hybridization solution, 1 million cpm of the labelled cDNA should be added. Incubate bag at 45° C. for 24–48 hours.
4. Remove membrane from bag and submerge in a wash solution containing 6× SSC, 0.2% SDS. Incubate at 45° C. for 30 minutes.
5. Measure radioactivity on the membrane using a geiger counter. If parts of the membrane which contain no DNA contain greater than 0.2 mREM/hr of radioactivity, wash the membrane for another 30 minutes with 6× SSC, 0.2% SDS. If a significant background radioactivity persists, begin washing the membrane with wash solution containing decreasing amounts of SSC (from 6× to 5× to 4×, etc.) while continuing to check the background radioactivity at 30 minute intervals.
6. As soon as the background radioactivity on the membrane is below 0.2mREM/hr, enclose it in plastic wrap to keep it moist. Then expose a piece of X-ray film to the membrane at −80° C. in complete darkness. Develop the film after 24 hours. If no hybridization to the immobilized DNA can be seen (successful hybridization appears as dark bands on the film) a longer exposure (up to 2 weeks) will be necessary. If too much hybridization is seen (as a dark smear over the immobilized DNA instead of discrete bands) then a shorter exposure should be done. If reduction in exposure time does not eliminate the problem, it will be necessary to wash the membrane in lower amounts of SSC following the procedure in step 5 and then re-exposing X-ray film to the membrane.

If discrete bands can be detected on the X-ray film, the *A. thaliana* cDNA can be used to directly identify a genomic clone from the chosen species containing a coding sequence homologous to the isolated *A. thaliana* cDNA coding Sequence and step II, infra, can be skipped. The number of digested DNA bands which hybridize to the *A. thaliana* cDNA provides an indication of the copy number of the homologous coding sequence in this species. If 1–2 bands of DNA digested with EcoRI, HindIII, or BamHI hybridizes to the *A. thaliana* cDNA, it is ,likely that the. copy number of the homologous coding sequence in.the chosen species is low (1–3 copies). Multiple hybridizing bands indicate a proportional increase in the copy number estimate.

II. IDENTIFICATION AND ISOLATION OF A cDNA HOMOLOGOUS TO THE ISOLATED *A. THALIANA* cDNA FROM THE CHOSEN SPECIES

The purpose of this step is to obtain a cDNA from a plant species of choice that is homologous to the *A. thaliana* cDNA coding sequence of FIG. 1. This cDNA can be used to identify a gene (including the promoter associated with the coding sequence) that is highly expressed in meristematic tissue and has a low copy number from the genome of the chosen species in step III, infra.

A. Isolation of RNA from meristem enriched tissue

The tissue chosen should be as enriched as possible in meristematic tissue. For most plant species young floral buds should suffice as an enriched source of meristematic tissue. The yield of RNA will vary but a sufficient quantity should be obtained from 10 grams of starting tissue.

The following solutions should be prepared:

Lysis buffer: Make up fresh and filter sterilize before each use, add first two components as powder, others from concentrated stocks.

1% Tri-iso-propylnapthalenesulfonic acid ammonium salt (SP/Kodak)
6% p-Aminosalicylic acid
100 mM Tris-HCl, pH 7.6
50 mM EGTA, pH 8.0
100 mM NaCl
1% SDS
50 mM 2-mercaptoethanol PCI: (phenol, chloroform, isoamyl) Combine equal volumes of chloroform:isoamyl alcohol (24:1) and tris saturated phenol.

When making up the necessary buffer and reagents it is necessary to use autoclaved or DEPC treated autoclaved water.

1. Freeze tissue in liquid nitrogen and grind in a mortar and pestle to a very fine powder.
2. Add the frozen powder to lysis buffer and PCI. Use 3–5 ml of buffer per gram of tissue and an equal volume of PCI.
3. Homogenize immediately with a polytron or the like.
4. Cfg.@room temperature, 12,000 g for 5 minutes to separate phases. Re-extract the aqueous phase with an equal volume of PCI and save the aqueous phase.
5. Add one-tenth volume of 3M Sodium Acetate (Na Acetate) and 2.5 volumes of ethanol to aqueous phase, mix. Store at –20° C. overnight or until frozen at –80° C.
6. Cfg@12,000 g for 25 minutes to sediment precipitate. Pour off supernatant.
7. Dissolve the pellet in water, using one half of the original lysis volume. When the pellet is in solution add an equal volume of cold 4M lithium chloride (LiCl). Place on ice at least 2 hours.
8. Cfg@room temperature, 12,000 g for 25 minutes.
9. Remove supernatant with care to avoid loss of the transparent RNA pellet. Allow tube to drain for 10 minutes.
10. Add one fourth of the original volume of water to dissolve the pellet. Then add an equal volume of cold 4M LiCl. Store on ice for at least 1 hour.
11. Repeat steps 8–10 above.
12. Repeat steps 8 and 9 again. Dissolve RNA in 0.9 ml of sterile water. Add 100 μl of 3M Na Acetate and 2.5 ml of ethanol. Store at –20° C. for at least 2 hours.
13. Cfg in microfuge tubes@15,000 rpm, 4° C. for 15 minutes. Remove supernatant and allow pellet to air dry for 5–10 minutes. Resuspend in 0.5–1 ml of sterile water.
14. Quantitate the RNA concentration by measuring the UV absorbance of an aliquot at 260 nm wavelength using a spectrophotometer. One O.D. unit of absorption at this wavelength represents 40 μg of RNA.

B. Making a cDNA library from RNA

1. First strand synthesis: Ten μl of Actinomycin D (400 μg/ml, Sigma) in 50% Ethanol (EtOH) is dried down in each reaction tube in a Savant speed vac. The following reagents are added to this tube (in the order given):

| Vol. | Substance | Final Conc. or Amount |
|---|---|---|
| 62 μl | Autoclaved Water (no DEPC) | |
| 10 μl | 10 × first strand buffer (see below) | |
| 10 μl | 5 mM dNTP | 500 μM each A, C, G, T (Sigma) |
| 10 μl | 100 μg/ml oligo d(pT) | 1 μg (Collaborative Research) |
| 2 μl | RNAsin (30 U/μl) (Promega) | 60 U |
| 2 μl | RNA | 1.5 μg |
| 3 μl | Reverse Transcriptase | 40 units (Life Sciences Corp., St. Petersburg, FL) |
| 2 μl | 32P-dATP | 200 Ci/mMole (Amersham Corp.) |

The reaction is incubated @42° C. for 60 minutes, then frozen on dry ice and stored at –20° C.

10× First strand buffer consists of:
500 mM Tris-HCl, pH 8.3
300 mM KCl
100 mM MgCl$_2$
4 mM DTT The quantity of cDNA synthesized is determined by precipitation of a portion of the reaction with trichloroacetic acid and scintillation counting.

2. Purification of the first strand:

Biogel P60 (100–200 mesh, Bio Rad, Richmond, Calif.) pre-swollen in 10 mM Tris-HCl/1 mM EDTA, pH 8.0 (TE buffer) is used to pour a column in a siliconized pasteur pipet plugged with siliconized glass wool (bed volume=1 ml). Wash the column with several volumes of 1 mM Tris pH 7.6/0.01 mM EDTA. Calibrate the column by running 90 μl of this same solution +10 μl column marker buffer (Column Marker buffer comprises: 5% Blue Dextran (2M dalton, Sigma) and 0.05% Phenol Red (or Bromphenol Blue at 0.1%) dissolved in 10 mM Tris, pH 7–8, 1 mM EDTA) over the column, noting when the blue dextran is eluted. Add more buffer to the column to elute the red dye.

Extract the first strand reaction twice with an equal volume of phenol. Add 0.5 μl of 2% bromphenol blue to the cDNA and load it on the column. Collect drops at the same time as the blue dextran eluted during calibration. The volume collected should be 250–300 μl.

3. Second strand synthesis and methylation

Dry the first strand to about 10 μl in a Savant speed vac or like apparatus.

Then add the following:

| Vol. | Substance | Final Conc. or Amount |
|---|---|---|
| 10 μl | cDNA | 700 ng or less |
| 10 μl | 10 × second strand buffer | 1× |
| 0.8 μl | 5 mM dNTP (N = A G, C, T) | 40 μM each |
| 2 μl | E. coli DNA PolI (NEB) | 20 units |
| 0.4 μl | E. coli DNA ligase (NEB) | 2 units |
| 0.5 μl | RNAase H (BRL) | 1 unit |
| 1 μl | BSA (1:10 dil. of BRL) | 50 μg/ml |
| — | water to 100 μl final volume | 1 U |
| 3 μl | 32P dCTP (optional) | 30 μCi |
| 1 μl | BSA (1:10 dil. of BRL) | 50 μg/ml |

NEB = New England Biolabs, Beverly, MA; BRL = Bethesda Research Labs, Gaithersberg, MD.

Incubate the reaction at 14° C. for 60 minutes, then at room temperature for 60 minutes.

10× Second Strand Buffer contains:
200 mMTris-Cl pH 7.4–7.5
50 mM MgCl$_2$ 1.0M KCl
100 mM Ammonium Sulfate
1.5 mM Beta-AND Add:
0.5 µl of 5 mM dNTP
1 µl of T4 DNA polymerase (NEB)

Incubate the reaction for 30 minutes at room temperature. Then add:
1.2 µl of 1 mM S-adenosyl L-methionine (Sigma)
1.0 µl ofEco RI Methylase (NEB)
2.4 µl of 0.5M EDTA Remove 5 µl from the reaction and add to 260 ng wild type lambda DNA (NEB) as a test reaction for methylation.

Incubate at 37° C. for 45 minutes.

Heat both the main and test reactions to 68° C. for 10 minutes to inactivate enzymes.

4. Assay for Completeness of methylation

To the heat treated test methylation add:
2 µl of high salt restriction buffer
12 µl of water
1 µl of EcoRI (20 units BRL)
0.5 µl of pUC 19 DNA (0.5 µg)
High salt restriction buffer=100 mM Tris-HCl, pH 7.6
100 mM $MgCl_2$
1.0M NaCl Incubate for 1 hour at 37° C.

Run on a 1% agarose gel along with 1 µg of undigested pUC19 DNA and lambda DNA digested with BsteII (NEB size markers). The pUC19 DNA in the reaction should be completely digested and the lambda DNA in the test reaction should be completely undigested. This shows that the methylase is effective in blocking the EcoRI sites in the cDNA from digestion.

5. Clean up double stranded cDNA

Extract the second strand reaction mixture twice with an equal volume of phenol. Add 0.5 µl of 0.2% bromphenol blue and run over a P60 column as above (see step 1, first strand synthesis) and dry to less than 5 µl in a speed vac.

6. Ligation of linkers to the cDNA

In a microfuge tube mix:
—µl of dscDNA (up to 5 µl or 500 ng)
2.5 µl of Phosphorylated Eco RI linkers (NEB, 250 ng)
1 µl of 10× Ligation buffer
1 µl of 10 mM ATP
µl of water (for final vol of 10 µl)
—1 µl of T4 DNA Ligase (–400 units NEB)

Incubate at 14° C. for 12 hours.

10× Ligation buffer:
300 mM Tris-Cl, pH 7.6
100 mM $MgCl_2$
50 mM DTT

7. Removal of linkers

Add to the ligation mix solution of #6 above:
2 µl of high salt restriction buffer
6 µl of water Heat to 68° C. for 10 minutes to inactivate ligase. Then add:
2 µl of EcoRI (40 units, NEB)

Incubate at 37° C. for 2.5 hours.

Then heat to 68° C. for 10 minutes to inactivate EcoRI.

8. Separate the cDNA from the linkers and purify

Add 5 µl of loading buffer to the digested cDNA/EcoRI linker reaction. Then electrophorese on a 0.8% Sea Plaque agarose (FMC Corp. Rockland, Md.)/TEA (40 mM Tris-Acetate/1.6 mM EDTA) minigel containing 0.3 µg/ml ethidium bromide. Run the gel at 4 V/cm until the bromphenol blue dye has migrated 4 centimeters. Lambda DNA digested with Hind III and EcoRI is also loaded onto the gel as a size marker. After electrophoresis the markers are visualized by UV fluorescence.

Loading Buffer contains:
250 mM of EDTA pH 7
0.2% of Bromphenol blue
50% of Glycerol Recover the cDNA from the gel using a DEAE membrane (NA45, available from Schleicher and Schuell). Pretreat membrane by the following method:

Place DEAE membrane in 10 mM Tris pH 7.6/10 mM EDTA for 10 minutes and then in 0.5M NaOH for 5 minutes. Rinse with distilled water and store (indefinitely) at 4° C. in 10 mM EDTA, pH ~7.5.

When the gel has run far enough (until Bromphenol Blue dye has run 4 cm) make a slit in the gel lane containing the cDNA sample at the lowest molecular weight required (500 bp) based on migration of the size markers in adjacent lanes and insert a piece of the DEAE membrane that is just slightly wider than the gel lane. Electrophorese the eDNA into the membrane. Remove the membrane from the gel. The area that has bound eDNA can be visualized by UV fluorescence due to the ethidium bromide in the gel. Trim away as much membrane as possible that does not have eDNA bound to it. Wash the membrane two times for 5 minutes in 5 millimeters of:
150 mM NaCl
20 mM Tris pH 8.0
0.1 mM EDTA Transfer to a microfuge tube and add 500 gl of:
1.0 M NaCl
20 mM Tris pH 8.0
0.1 mM EDTA and heat to 55° C. for 25 minutes. Remove the supernatant which now contains about 70% of the cDNA. The rest is lost on the membrane. Spin the tube for 5 minutes in a microfuge to remove any possible traces of membrane pieces and transfer the supernatant to a clean tube.

9. Ligation of cDNA to lambda ZAP or equivalent

Add 2 µl (2 µg) of lambda ZAP arms (Stratagene) or an equivalent to the cDNA. The lambda ZAP arms contain the pBluescript sequences. Then add 1 ml of cold EtOH and chill at –80° C. for 1 hour. Centrifuge at 15,000 rpm for 15 minutes. Drain the tube and wipe out the inside with a sterile swab carefully avoiding the pellet (which may be invisible). Rinse with 200 µl of 70% ethanol chilled to –20° C. without disturbing the pellet. Let the pellet air dry 30 minutes.

Add to the dried pellet:
7.2 µl of Water
1 µl of 10× Ligation Buffer
1 µl of 10 mM ATP
0.8 µl T4 DNA Ligase Incubate 20 hours at 14° C.

10× Ligation Buffer comprises:
200 mM Tris-HCl, pH 7.6
100 mM $MgCl_2$
50 mM DTT 10. Packaging ligated cDNA The cDNA is now ready for packaging and plating into bacteriophage. Package one fourth (2.5 µl) of the ligation reaction in vitro into phage using Gigapack packaging extracts (Stratagene Cloning Systems, San Diego, Calif.) or an equivalent according to the manufacturer's instructions.

11. Plating the packaged cDNA

Grow 2 ml of *E. coli* strain BB4 in TB media supplemented with 0.2% maltese and 10 mM magnesium sulfate to an O.D. 600 of 0.5. Transfer 600 µl to a 10 ml tube and add 1 µl of the packaged cDNA. Incubate for 15 minutes at 37° C. while gently shaking. Then add 4 ml of melted top agar (48° C.), 50 µl of 0.5M IPTG, and 50 µl of 250 mg/ml X-Gal. Pour immediately and evenly onto a 15 cm NZY agar plate. Incubate at 37° C. After 6 hours plaques should be visible. White plaques represent packaged cDNA's and should be 10–100 fold more abundant than blue plaques representing lambda-ZAP containing no cDNA insert. Calculate the number of plaques to use as a quantitation of the cDNA library.

TB media:
5 g/l NaCl
10 g/l Bacto-tryptene

Dissolve in water, autoclave to sterilize.

NZY plates:
5 g/l NaCl
2 g/l hydrated magnesium sulfate
5 g/l yeast extract
10 g/l NZ Amine-(casein hydrolysate)
15 g/l Difco agar Dissolve in water, autoclave to sterilize.

Pour about 80 ml/15 cm plate.

Top agar: Same as NZY plates but substitute agar with 0.7% agarose. Cool to 48° C. before use.

C. Identification of a DNA coding sequence from the chosen snecies homologous to the isolated *A. thaliana* coding sequence 1. Immobilizing cDNA onto nitrocellulose Using the procedure described above, step B-10, make 10 plates (15 cm) with about 15,000 cDNA plaques per plate. Incubate plates until plaques are clearly visible (8 hours). Then for each plate place a nitrocellulose filter (cut to the plate's form) in contact with the top agar for 1 minute. Make corresponding marks on each filter and plate so that the filters can be later realigned to the plates in the same configuration. Remove the filters carefully (avoid disturbing top agar) and immerse them in denaturant (0.1N NaOH, 1.5M NaCl). After 3 minutes transfer the filters to neutralizer solution (0.2M Tris-HCl, pH 7.6/2× SSC) for 5 minutes. Rinse filters after neutralization in 2× SSC and place on Whatman 3MM paper to air dry for 5 minutes. Next wrap filters in between sheets of Whatman filter paper and bake for 2 hours at 80° C. Duplicate filters can be made for each plate as well by repeating the procedure above with the exception that the filters are left in contact with the top agar for 3 minutes instead of 1 minute.

2. Hybridizing the cDNA library of the chosen plant species to *A. thaliana* cDNA Make radiolabelled *A. thaliana* cDNA according to the protocol described in step I-D, supra. Place filters in a sealable bag and add just enough hybridization buffer to completely immerse them. Seal the bag and incubate at 45° C. for at least 4 hours. Then add the radiolabelled cDNA to the bag (1 million cnts/ml) after boiling it for 8 minutes. Incubate for 24–48 hours at 45° C..

Remove the filters from the bags and submerge in wash solution containing 6× SSC, 0.2% SDS, Incubate at 45° C. for 30 minutes. After this incubation measure the radioactivity remaining on the filters using a geiger counter. If there is a general level of radioactivity across each filter that is greater than 0.2 mREM/hr, wash the filters for another 30 minutes with 6× SSC, 0.2% SDS. If the radioactivity across each filter is still greater than 0.2 mREM/hr begin washing the filters with wash solution containing decreasing amounts of SSC (from 6× to 5× to 4×, etc.) while continuing to check radioactivity at 30 minute intervals.

When the radioactivity across the filters falls below 0.2 mREM/hr, enclose them in plastic wrap and keep moist. Then expose a piece of X-ray film to the filters at −80° C. in complete darkness. After a 24 hour exposure, develop the film. Before removing the film from contact with the filters, mark the film so that it can be realigned with the filters after developing. If no hybridization is apparent a longer exposure (up to 2 weeks) will be necessary. If too much hybridization is seen (as dark staining across the whole filter area) then a shorter exposure should be done. If reduction in exposure time does not eliminate the problem, it will be necessary to wash the filters in lower amounts of SSC as described in the previous paragraph and then re-exposing them to X- ray film.

These adjustments should result in the visualization of dark spots on the X-ray film corresponding to cDNA from individual plaque(s) on the filter. These dark spots represent specific hybridization of the *A. thaliana* cDNA to a plaque(s) containing a homologous cDNA from the chosen species. Using the alignment marks, it is possible to identify the intact plaques on the original plates corresponding to cDNA hybridization. These plaques are removed from the plates with the small end of a pasteur pipette and placed into a microfuge tube containing 1 ml of SM buffer. The phage are eluted from the agar into the SM by incubation for 2 hours at room temp. The eluted phage are probably not completely pure at this stage, containing contaminating phage that were adjacent to the target phage (containing the cDNA) on the plate.

In order to purify the phage containing the cDNA further, another round of plating/hybridization is performed. Following the procedure in B-10 and C,-supra, each eluted phage is plated on a single plate at a low concentration (100–1000 plaques/15 cm plate), filters are made, and hybridized to the *A. thaliana* cDNA in order to identify well separated plaques containing homologous cDNAs. One well isolated plaque from each plate is removed and eluted into 1 ml of SM buffer as above. This eluted phage should be pure enough to proceed to the next cloning step. An aliquot (5–10 µl) should be plated in order to quantitate the number of plaque forming units(pfu) per microliter.

SM buffer:
5.8 g/l NaCl
2.0 g/l magnesium sulfate
50 ml 1M Tris-HCl, pH 7.5
5 ml 2% gelatin Dissolve in water, autoclave to sterilize.

D. Transfer of the cloned cDNA into *E. coli*

1. I In a 50 ml conical tube combine:
   200 µl of *E. coli* strain XL1-Blue cells grown in TB media to OD600=1.0
   200 µl of purified, eluted phage from previous step which should contain at least 100,000 pfu
   10 µl of R408 helper phage containing at least 10,000 pfu Incubate at 37° C. for 15 minutes.

2. Add 5 ml of 2XYT media and incubate 4–6 hours at 37° C. with shaking.

2XYT media comprises: 10 g/l NaCL, 10 g/l yeast extract and 8 g/l Bacto-tryptone.

3. Heat tube at 70° C. for 20 minutes, then spin tube for 5 minutes at 1000 g. Transfer supernatant to a sterile tube. This supernatant contains the packaged pBluescript plasmid with cDNA insert in M13 or f1 phage particles.

4. Combine the following in two tubes:
   200 µl of *E. coli* strain XL1-Blue cells grown in TB media to OD600=1.0
   200 µl of phage stock from step 3 above (tube 1) or 2 µl of phage stock from step 3 (tube 2)
   Incubate tubes at 37° C. for 15 minutes.

5. Plate 50 µl from each tube onto L-broth plates containing 200 µg/ml of Ampicillin. Incubate overnight at 37° C. Colonies appearing on the plates should contain the pBluescript plasmid with the cDNA insert. Pick a well separated colony with a sterile toothpick and transfer to a tube containing 2 ml of L-broth and 200 µg/ml ampicillin. Incubate at 37° C. while shaking until the culture is saturated (6-12 hours). Then combine 1 ml of the culture and 1 ml of sterile glycerol in a screwcap glass vial, mix, and freeze at -80° C. This can serve as a stock culture of the homologous cDNA from the chosen plant species in *E. coli*.

L-broth contains:
   10 g/l Bacto-tryptone
   5 g/l yeast extract
   10 g/l NaCl E. Characterization of the cDNA insert from *E. coli*
   1. Isolate plasmid DNA Grow a 2 ml culture of *E. coli* containing the pBluescript plasmid with the cDNA insert in L-broth+200 µg/ml ampicillin from a stock.

Incubate at 37° C. while shaking until the culture is saturated (overnight). Then transfer 1.5 ml of culture to a microfuge tube and cfg for 15 seconds to pellet cells. Pour off the supernatant and resuspend the cell pellet in 100 µl of solution 1. Add 200 µl of solution 2, mix, and incubate on ice for 5 minutes. Then add 150 µl of solution 3, mix, and incubate on ice for 30 minutes. Cfg for 5 minutes. Transfer supernatant to a clean tube containing 0.5 ml of Tris-saturated phenol, mix. Cfg for 5 minutes. Carefully remove upper phase and transfer to a microfuge tube containing 1 ml of ethanol and incubate on dry ice for 30 minutes. Cfg for 5 minutes to pellet DNA. Remove supernatant and let pellet air dry. Dissolve pellet in 50 µl of water +1 µl of RNase (0.1 µg/ml). This plasmid DNA should be at a concentration of about 0.2 µg/µl.

Solution 1:
   50 mM glucose
   10 mM EDTA
   25 mM Tris-HCl (pH 8.0)

Solution 2:
   0.2N NaOH
   1% SDS

Solution 3: 3M potassium acetate
   115 µl/ml of glacial acetic acid

2. Restriction mapping of the cDNA insert

Digest the plasmid DNA with several restriction enzymes including EcoRI, HindIII, BamHI, PstI, and XbaI under conditions supplied by the manufacturer. Each digest should include 5 µl of plasmid DNA and 10 µl total volume. Add 1 µl of loading buffer to each digested DNA and electrophorese on a 0.8% agarose/TEA (40 mM Tris acetate, 1.6 mM EDTA) minigel containing 0.3 µg/ml ethidium bromide. Lambda DNA digested with BstEII is co-electrophoresed as a size marker. Run the gel at 4 V/cm until the bromphenol blue has migrated 7 cm. Visualize the DNA bands under UV fluorescence and photograph. The size of the digested DNA fragments can be determined by comparison with the known sizes of the digested lambda DNA fragments. The size of the cDNA insert and the location of restriction sites within it can be determined by comparing the sizes of the restriction fragments with the known restriction map of the pBluescript plasmid.

The size of the cDNA insert should be at least 1.0 kb. If it is smaller, a larger insert containing the entire cDNA must be isolated. The entire cDNA is required so that the 5' end adjacent to the promoter is present. This end of the cDNA can be sequenced and subsequently used to pinpoint the junction of the promoter/leader to the coding sequence.

3. Sequencing the 5' end of the cDNA

The plasmid DNA can be sequenced by the dideoxy method of Sanger et al. (1977), using a sequencing kit available from U.S. Biochem. Co. according to the manufacturer's instructions or by any method of preference. Sequencing with the M13 -20 primer (Stratagene) will provide sequence of either the 5' or 3' end of the cDNA, depending on its orientation in the pBluescript plasmid. If 3' sequence is obtained, repeat sequencing using the reverse primer (Stratagene) to obtain 5' end sequence. The 5' end sequence should be compared to the isolated *A. thaliana* cDNA to locate the 5' end of the coding sequence. Once the cDNA insert has been oriented, a restriction fragment observed in step 2 above between 0.5-1.0 kb encompassing the 5' end should be identified. If such a fragment does not exist further restriction mapping using other enzymes should be performed until one is identified. This fragment will be suitable for isolating and radiolabeling to probe for the promoter of the homologous cDNA in the genome of the chosen plant species (step III).

III. IDENTIFICATION AND ISOLATION OF THE PROMOTER OF THE HOMOLOGOUS cDNA FROM THE GENOME OF THE CHOSEN SPECIES

Making a library of genomic fragments cloned into phase
   1. Perform a partial digestion of genomic DNA with MboI:
      To a microfuge tube add:
         10 µg of genomic DNA of chosen species (see I-A)
         10 gl of 10× enzyme buffer (as suggested by enzyme supplier)
         10 units of MboI restriction enzyme (New England Biolabs)

Add water to final volume of 100 µl. Incubate tube at 37° C. At 1 minute intervals transfer a 10 µl aliquot of the reaction mix to a clean tube, add 1 µl loading buffer, and place on ice. After all of the reaction mix has been aliquoted and put on ice, load all the aliquots onto a 0.8% agarose gel along with 1 µg of lambda DNA digested with 1) BstEII and 2) HindIII and electrophorese at 4 V/cm until the bromphenol blue dye has migrated about 6 cm. Then visualize the DNA by observing the gel under UV light. Using the digested lambda DNA as size markers, determine which aliquot contains the most genomic DNA between 14 and 23 kb. This aliquot represents the optimal partial digestion time.

2. Isolate partial MboI digested genomic DNA
      To a microfuge tube add:
         25 µg of genomic DNA of chosen species (see I-A)
         25 µl of 10× enzyme buffer (suggested by enzyme supplier)
         25 units of MboI restriction enzyme (New England Biolabs)

Add water to final volume of 250 µl. Incubate tube at 37° C. for the optimal partial digestion time (see above). Add 25 µl of loading buffer and load onto a 0.8% agarose gel with lambda size markers and electrophorese as described in step 1, supra. When the gel has run far enough (until the Bromphenol Blue dye has run at least 6 cm) make a slit in the gel lane(s) containing the genomic DNA sample at the lowest molecular weight required (14 kb) based on migration of the size markers in adjacent lanes and insert a piece of pretreated DEAE membrane (NA45, see step IIB-8) that encompasses the gel lane(s). Electrophorese the DNA into the membrane until the 23 kb lambda HindIII marker is adjacent to the membrane. Remove the membrane from the gel. The area that has bound DNA can be visualized by UV fluorescence due to the ethidium bromide in the gel. Trim away as much membrane as possible that does not have cDNA bound to it. Wash the membrane twice for 5 minutes in 5 ml of:

150 mM NaCl
20 mM Tris pH 8.0
0.1 mM EDTA

Transfer to a microfuge tube and add 500 µl of:
1.0M NaCl
20 mM Tris pH8.0
0.1 mM EDTA Heat to 55° C. for 25 minutes. Remove the supernatant which now contains about 70% of the DNA. The rest is lost on the membrane. Spin the tube for 5 minutes in a microfuge to remove any possible traces of membrane pieces and transfer the supernatant to a clean tube.

Add 2 µl (2 µg) of lambda GT10 phage arms (Stratagene) or an equivalent to the tube. Then add 1 ml of cold EtOH and chill at −80° C. for 1 hour. Centrifuge at 15,000 rpm for 15 minutes. Drain the tube and wipe out the inside with a sterile swab carefully avoiding the pellet (which may be invisible). Rinse with 200 µl of 70%ethanol chilled to −20° C. without disturbing the pellet. Let the pellet air dry 30 minutes.

Add to the dried pellet:
7.2 µl of Water
1 µl of 10× Ligation Buffer
1 µl of 10 mM ATP
0.8 µl T4 DNA Ligase Incubate 20 hours at 14° C.
10× Ligation Buffer
200 mM Tris-HCl pH 7.6
100 mM $MgCl_2$
50 mM dithiothreitol 3. Packaging and plating the ligated genomic DNA These steps are performed as outlined for cDNA in steps I-B10 and 11, supra, except that E. coli strain C600 is used in place of strain BB4.

B. Identification of a homologous gene from the genomic library

Follow the protocol outlined in step II-C, supra, with the following exceptions:

1. About 1 million plaques containing genomic DNA should be plated onto 20 plates (50,000 plaques/15 cm plate).
2. If a cDNA from the chosen species homologous to the cDNA from A. thaliana is isolated, it should be radiolabelled and hybridized to the genomic library. Otherwise the A. thaliana cDNA should be used.
3a. If a cDNA from the chosen species is used to probe the genomic library, hybridization should be performed at 65° C. After hybridization, the filters should be washed first for 1 hour in 2× SSC at 65° C. and then for 30 minutes in 0.2× SSC at 65° C. before they are used to expose X-ray film. More stringent hybridization and wash conditions are possible when using a cDNA probe from the same species as the genomic library.
3b. If the A. thaliana cDNA is used to probe the genomic library, hybridization should be performed at 45° C. After hybridization, the filters should be washed in the same manner that was used to obtain discrete bands on the Southern blot in step I.

This procedure allows identification of plaques containing the gene of interest which are used in the next step.

C. Cloning the promoter region from identified phage

1. Isolating phage DNA containing the desired gene DNA should be isolated from one or two identified phage.

To a 5 ml culture tube add:
150 µl of a saturated overnight culture of E. coli strain C600
10 million pfu of eluted phage Incubate at 37° C. for 30 minutes with gentle shaking. Add 4 mls of L-broth and incubate cultures at 37° C. with shaking until the culture clears (about 5 hours). Then add 100 µl of chloroform to the tube and continue 37° C. incubation for 15 minutes. Allow chloroform to settle before proceeding.

Transfer lysate to a 12 ml polypropylene culture tube. Cfg at 5,000 rpm for 10 minutes in a Sorvall ss34 rotor or equivalent. Transfer lysate into a 5 ml thick-walled polycarbonate tube for the Beckman 50.3 Ti rotor or equivalent being careful to avoid carrying any chloroform along. Add 5 µl of DNase @1 mg/ml and 10 µl of RNase @2 mg/ml. Mix and incubate on ice overnight. Cfg at 40,000 rpm for 1 hour, 4° C. Remove supernatant and leave the tube exposed to air until completely dry (30 minutes). Resuspend the pellet in 0.41 ml of SM buffer. Transfer 0.4 ml to a microfuge tube and allow to warm to room temperature.

Add to the tube:
1.5 µl of diethylpyrocarbonate (DEPC)
10 µl of 10% SDS
90 µl of Tris/EDTA (combine 1 ml of 2M Tris, unadjusted for pH, with 0.8 ml of 0.25M EDTA pH 8.0).

Mix and place closed tubes @70° C. for 10 minutes. Remove and allow tube to cool to room temperature. Then add 50 µl of 5M potassium acetate and mix. Incubate on ice 30 minutes. Then cfg @15,000 rpm, 4° C. for 15 minutes. Carefully transfer supernatant to a clean tube. Repeat cfg and transfer. Then add 1 ml of 95% ethanol and mix. Cfg for 5 minutes, remove supernatant, and wash pellet with 80% ethanol. Allow pellet to air dry. Resuspend pellet in 200 µl of TE(pH 8.0) plus 0.3M sodium acetate. Then add 400 µl of ethanol and mix. Cfg for 5 minutes, remove supernatant, and wash pellet with 80% ethanol. Allow pellet to air dry. Dissolve pellet in 38 µl of TE(pH 8.0) and 2 µl of RNase @2 mg/ml. The tube should contain 4–8 µg of phage DNA.

2. Identification of a genomic restriction fragment likely to contain the gene promoter by southern hybridization Digest the isolated phage DNA with each of the following restriction enzymes: EcoRI, HindIII, BamHI, PstI, XbaI, and SalI. For each digestion use:
2 µl of isolated phage DNA.

2 µl of 10× restriction buffer (as suggested by the manufacturer)
1 µl of concentrated restriction enzyme
15 µl of water Incubate digestions at 37° C. for 3 hours. Then electrophorese the digested DNA across an agarose gel, immobilize it onto nylon membrane, and hybridize with either 1) a labelled 0.3–1.0 kb DNA fragment encompassing the 5' end of the cDNA from the chosen species (stepIIE-3) or 2) a labelled 0.3 kb BamHI-NcoI DNA fragment from pMON648 encompassing the 5' end of the cDNA. Use the protocol detailed in I-B through I-D. Use the guidelines in B-3a or B-3b above (whichever is applicable) for hybridization and washing conditions.

Using this procedure it should be possible to identify a restriction fragment between 5 and 10 kb in size which contains the desired coding sequence. A fragment this large will probably also contain the region adjacent to the. 5' end of the coding sequence constituting the promoter to this region.

3. Cloning the genomic fragment likely to contain the desired promoter into *E. coli.*

Transformation of *E. coli* can be accomplished by standard methods. Described below is a general method that is applicable.

Grow a culture of the desired *E. coli* strain to saturation in L-broth. Cfg culture at 10,000 g for 5 minutes to pellet cells. Remove supernatant and resuspend cells in ½ of original volume with cold 50 mM calcium chloride.. Incubate on ice 30 minutes, then Cfg at 8000 g for 5 minutes. Remove supernatant, resuspend pellet in 1/10 of original volume with cold Calcium Chloride. Cells are now competent for transformation.

Into a sterile microfuge tube add 1 µl of plasmid DNA or ligated DNA and 200 µl of competent cells (see above). Incubate on ice for 30 minutes. Place in a 42° C. waterbath for 90 seconds, then back on ice for 1 minute. Add 1 ml of L-broth. Cfg for 15 seconds to pellet cells. Pour off supernatant, leaving about 100 µl. Resuspend pellet in remaining supernatant and plate onto L-agar+the appropriate antibiotic to select for cells containing the desired plasmid DNA. Incubate at 37° C. overnight. Colonies appearing on selection plate can be screened for the presence of the desired plasmid.

Repeat the restriction digest in step 2 which produced the restriction fragment between 5 and 10 kb in size which hybridized to the probe using 5 µl of phage DNA. Isolate this fragment from an agarose gel using DEAE cellulose as described in step IIIA-2 except that no phage DNA is added before ethanol precipitation. Resuspend the DNA in 20 µl of water.

Digest 1 µg of pUC119 DNA with the same restriction enzyme used to isolate the fragment above under the same conditions. Following digestion, add 1 unit of calf alkaline phosphatase (Boerhinger Mannhelm) and incubate at 37° C. for 30 minutes. Then add sodium acetate to a final concentration of 0.3M and 2 volumes of ethanol. Chill on dry ice and cfg @ 15,000 rpm for 10 minutes in a microfuge to pellet the DNA. Remove the supernatant, wash the pellet with 80% ethanol and let air dry. Dissolve the DNA in 20 µl of water.

In a microfuge tube add:
1 µl of digested, phosphatased pUC119 DNA
5 µl of the purified restriction fragment
3 µl of 10× Ligation Buffer
3 µl of 10 mM ATP
2 µl of T4 DNA Ligase
16 µl of sterile water Incubate overnight at 14° C. Transform into *E. coli* strain JM101 and spread over a plate containing L-agar plus 200 µg/ml ampicillin X-gal. Incubate the plate at 37° C. overnight. Non-blue colonies which appear on the plate should contain the gene fragment inserted into pUC119. Grow 2 ml cultures of 10 of these colonies and prepare miniprep plasmid DNA from them (step IIE-1). Identify and map a plasmid containing the gene insert by restriction digestion and Subsequent electrophoresis. It may be possible to tentatively-identify the specific region in the genomic fragment which contains the gene by comparing its restriction map with that of the cDNA, 4. Identifying the promoter-leader/coding sequence junction Repeat steps 2 and 3 above using the plasmid DNA from step 3 to identify and clone a smaller restriction fragment (2 kp or less) which hybridizes to the 5' end of the cDNA. Sequence this cloned DNA by the dideoxy method using a sequenase kit available from U.S. Blochem. Co. according to the manufacturer's instructions or by any other preferred method. Sequencing with the M13 −20 primer and the reverse primer (Stratagene) will provide sequence from both ends of the cloned DNA. Comparison of the sequence obtained with the *A. thaliana* gene or the homologous cDNA (if available) should allow identification and orientation of the gene within the genomic fragment. This information is used to determine where the promoter-leader/coding sequence junction is in the genomic fragment. If this sequence is not included, continue sequencing with 20 nucleotide primers made identical to the end of the previous sequence until it is obtained. These primers can be ordered from Pharmacia LKB or any other preferred supplier.

The size of the region 5' to the coding sequence in the isolated genomic fragment(s) should be determined from the location of the leader/coding sequence junction. If this region is less than 2 kp, it will be necessary to isolate another genomic fragment containing a larger region upstream of the coding sequence. This is accomplished by repeating step C with another phage from step B until one containing this upstream region is identified.

5. Introducing a convenient restriction site at the promoter leader/coding sequence junction
   a. Mutagenesis primer—Using the junction sequence obtained in step 4, obtain a synthetic oligonucleotide that contains 20 nucleotides of homology spanning the leader/coding sequence junction with a restriction enzyme recognition sequence inserted into the leader immediately adjacent to the start of the coding sequence (Pharmacia LKB or any preferred supplier). Choose an enzyme recognition sequence that can be conveniently used to subclone a promoter-leader fragment at least 1 kb in size from the total genomic fragment, i.e. one that is not present in the promoter region.
   b. Single stranded template prep—Transform the pUC119 plasmid containing the gene insert from step 3 into *E. coli* strain BW313. Use this to inoculate 2 ml of L-broth+200 µg/ml ampicillin. Incubate at 37° C., shaking until the culture is slightly turbid (about 50 Klett units). Then add helper phage M13K07(ca. 10 million pfu) and continue 37° C. incubation overnight.

Aliquot 1.5 ml of culture into a microfuge tube. Cfg for 15 seconds and transfer supernatant into a clean tube. Cfg for 5 minutes and transfer 1.2 ml of supernatant into clean tube. Add 180 µl of 2.5M NaCl, 20% polyethylene glycol, mix thoroughly. Incubate at room temp. for 15 minutes. Cfg for 5 minutes, discard supernatant completely. Resuspend pellet in 200 µl of TE buffer. Heat for 5 minutes @55° C., mix. Add 100 μl of phenol, mix. Heat for 5 minutes @55° C. Add 100 μl of chloroform, mix. Leave at room temperature for 5 minutes. Mix well, then cfg for 5 minutes. Transfer 160 μl of upper phase into a new tube. Add 20 μl of 3N sodium acetate (pH 4.5) and 400 μl of cold ethanol into new tube. Chill on dry ice, then cfg for 5 minutes. Remove supernatant, add 200 μl of 80% ethanol, cfg 5 more minutes. Remove supernatant and let air dry. Resuspend pellet. in 20 μl of TE, electrophorese 2 μl on agarose gel to quantitate (compare UV intensity with known amount of DNA).

c. Kinasing mutagenesis primer
To a microfuge tube add:
   50 pmol of mutagenesis primer
   1 μl of 10× ligation buffer
   10 mM ATP
   1 μl of Kinase (10 units)
Add water to 10 μl final volume. Incubate at 37° C. for 30 minutes, then at 70° C. for 5 minutes.

d. Annealing template to primer
To a microfuge tube add:
   500 ng of template (b)
   2 μl of kinased mutagenesis primer (c)
   2 pμl of 10× Hin buffer
Add water to 20 μl total volume. Place sample in a beaker of water @90° C., let cool to room temperature.
10×Hin buffer contains:
   66 mM Tris, pH 7.4
   66 mM NaCl
   66 mM magnesim dichloride
   50 mM DTT.

e. Fill-in reaction
To a microfuge tube add:
   20 μl of NTP mix
   20 μl of annealed template primer (d)
   3 gl of T4 ligase (about 1000 units)
   2 μl of DNA polymerase, klenow enzyme (about 10 units)
Incubate overnight at 15° C.
Add 2 μl more of T4 ligase, incubate 2 more hours at 15° C.
NTP mix:
   6 gl of 10× Hin buffer
   12 gl of 5 mM dATP
   12 μl of 5 mM dCTP
   12 μl of 5 mM dGTP
   12 μl of 5 mM dTTP
   6 μl of 10 mM ATP f. Transformation
Use 20 μl of the fill-in reaction (e) to transform *E. coli* strain JM101. Cells are plated onto L-agar +200 μg/ml ampicillin. Some of the colonies which grow on this plate should contain the desired pUC119 gene plasmid from step C-3 with the mutagenesis primer (a) incorporated.

g. Screening for desired plasmid
Plasmid DNA is made from ampicillin resistant colonies (f) using the protocol in step IIE-1. This DNA is digested with the restriction enzyme which recognizes the sequence incorporated into the mutagenesis primer (a) and run on an agarose gel. In this way a plasmid which is cut at the promoter-leader/coding sequence junction with this enzyme can be identified. Sequence surrounding the mutagenesis site on the plasmid should then be verified.

6. Isolating the promoter region
Using the information obtained from mapping the promoter region, digest the plasmid DNA from step 5(g) above with restriction enzymes which will release a promoter fragment starting at the leader/coding sequence junction and extending at least 1 kb upstream. This fragment can be isolated from agarose gel using DEAE cellulose as described in step IIIA-2 except that no phage DNA is added before ethanol precipitation.

The isolated fragment can be utilized in a selected chimeric gene construction, cloned into any desired vector and transformed into plant cells to express a selected heterologous structural coding sequence in meristematic and/or rapidly dividing cells.

A promoter region isolated from *A. thaliana* was operably linked to reporter genes and transformed into plant cells to test the activity of the promoter region. Any promoter region isolated pursuant to this invention can be tested in a similar manner. Transformed plants containing a promoter region that directs high levels of transcription of a heterologous gene to which it is operably linked can be obtained by standard methods known to those skilled in the art.

A typical chimeric gene to be transformed into a plant of choice will include a promoter region, a heterologous structural coding sequence and a 3' non-translated polyadenylation site. A heterologous structural coding sequence means a structural coding sequence that is not native to the plant being transformed or a structural coding sequence that has been engineered for improved characteristics of its protein product. Heterologous with respect to the promoter means that the coding sequence does not exist in nature in the same gene with the promoter to which it is now attached. Chimeric means a novel non-naturally occurring gene which is comprised of parts of different genes. In chimeric genes utilizing the promoter of the present invention any type of heterologous structural coding sequence can be utilized to obtain the trait or characteristic desired. The 3' non-translated region contains a polyadenylation signal which functions in plants to cause the addition of polyadenylate nucleotides to the 3' end of the viral RNA. Examples of suitable 3' regions are (a) the 3' transcribed, non-translated regions containing the polyadenylation signal of the tumor-inducing (Ti) plasmid genes of Agrobacterium, such as the nopaline synthase (NOS) gene, and (2) plant genes like the 7s soybean storage protein genes and the pea E9 small subunit of the RuBP carboxylase gene.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be part of the 5' end of the non-translated region of the native coding sequence for the heterologous coding sequence, or part of the promoter sequence, or can be derived from an unrelated promoter or coding sequence as discussed above.

A DNA construct of the present invention can be inserted into the genome of a plant by any suitable method. Suitable plant transformation vectors include those derived from a Ti plasmid of *Agrobacterium tumefaciens,* such as those disclosed by Herrera-Estrella (1983), Bevan (1983), Klee (1985) and EPO publication 120,516 (Schilperoort, et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, particle gun technology, and transformation using viruses.

The construction of vectors capable of being inserted into a plant genome via *Agrobacterium tumefaciens* mediated delivery is known to those of ordinary skill in the art. Typical plant cloning vectors comprise selectable and scoreable marker genes, T-DNA borders, cloning sites, appropriate bacterial genes to facilitate identification of transconjugates, broad host-range replication and mobilization functions and other elements as desired.

If Agrobacterium mediated delivery is chosen, once the vector has been introduced into the disarmed Agrobacterium strain, the desired plant can then be transformed. Any known method of transformation that will work with the desired plant can be utilized. These methods include the leaf disc method of Horsch et. al (1985) and as adapted by Fry et al. (1986) for *Brassica napus*.

Suitable plants for the practice of the present invention include, but are not limited to, soybean, cotton, alfalfa, oilseed rape (including canola), flax, tomato, sugar beet, sunflower, potato, tobacco, maize, wheat, rice petunia, celery, cucumber, *Medicago varia*, lotus, *Vigna aconitifolia*, carrot, cauliflower, horseradish, morning glory and lettuce.

In the examples that follow, tobacco plants were transformed by the following method.

Tobacco (*Nicotiani tabacum var. samsun*) leaf disks with diameters of about 6 mm were taken from surface sterilized tobacco leaves. These were cultivated on MS104 agar medium for two days to promote partial cell wall formation at the wound surfaces. They were then submerged in a culture of *A. tumefaciens* cells containing the plasmid with the chimeric gene of interest and pMP90RK which had been grown overnight in Luria broth at 28° C., and shaken gently. The cells were. removed from the bacterial suspension, blotted dry, and incubated upside down on filter paper placed over "nurse" cultures of tobacco cells as described by Horsch (1980). After two or three days, the disks were transferred to petri dishes containing MS media with 500 µg/ml carbenicillin with no nurse culture.

Control tissue was created using *A. tumefaciens* cells containing the helper plasmid pMP90RK and a different plant transformation vector, pMON505, which contained a T-DNA region with a NOS/NPTII/NOS kanamycin resistance gene and a NOS selectable marker gene identical to that in the plasmid with the chimeric gene of interest, but without the meristematic promoter/reporter gene.

Within ten days after transfer to the MS media, actively growing callus tissue appeared on the periphery of all disks on both the control and transformed plates.

Transformed tobacco plants were produced by regeneration from the above-described transformed leaf disks by the procedure described by Horsch et al. (1985).

Brassica napus plants were transformed according to the following method. The cloning Vector was introduced into the plant by the method of Fry et al. (1986). Four terminal internodes from plants just prior to bolting or in the process of bolting, but before flowering were removed and surface sterilized in 70° C. v/v ethanol for one minute, 2% w/v sodium hypochlorite for twenty minutes, and rinsed three times in sterile distilled water. Stem segments were cut into 5 mm discs (Stringam 1977) and placed in a sterile 15×100 mm petri plate, noting the orientation of the basal end. The discs were inoculated for five minutes by pouring two to four milliliters of an overnight culture of the ACO *A. tumefaciens* strain containing the plasmid containing the chimeric gene of interest with the meristematic promoter over the discs in the petri plato and then blotted dry by placing sterile filter paper in the petri plate and turning the plate over to absorb any excess bacteria. The stem discs were placed basal side down on feeder plates on medium containing 1/10× standard MS salts, B5 vitamins, 3% sucrose, 0.8% agar, pH 5.7, 1 mg/l BA and 1.4 ml TXD feeder Cells (Horsch et al. 1985)

After a two to three day coculture period, stem discs were transferred, five to a deep dish petri plate (25×100 mm) containing the same medium with standard MS salts, 1 mg/l BA, 500 mg/l carbenicillin, 0.3 mm arginine, and 100 mg/l kanamycin for selection. At three weeks the stem explants were transferred to fresh plates containing the same medium. Culture of the explants was in a growth room under continuous cool white light at 26° C. Shoots that developed in the next one to three week period were excised from the stem explants, dipped in Rootone® and placed in 2½ inch pots containing water saturated Metro Mix 350 in closed GAF containers for ten days in a chamber with a constant temperature of 21° C. and a 16 hour photoperiod. The shoots are assayed for the presence of kanamycin resistance immediately after being excised from the stem explant while still sterile.

The embodiments described above and the following examples are provided to better elucidate the practice of the present invention. It should be understood that these embodiments and examples are provided for illustrative purposes only, and are not by way of limitation of the scope of the invention.

EXAMPLE 1

As previously described, a 4 kb BamHI fragment from pMON648 containing the *A. thaliana* promoter region was inserted into the BamHI site of pUC119 to create pMON1575. A BglII site was then introduced into pMON1575 at the junction of the *A. thaliana* promoter-leader sequence and its corresponding coding sequence by site directed mutagenesis to create pMON1576. The oligonucleotide primer used for this mutagenesis consisted of the following sequence (5'–3'):

GAAAGGAGACAT<u>AGA</u>TCTTTGTGTGTG

The underlined nucleotides were inserted to create the BglII site. The 2.4 kb BglII-StuI fragment from pMON1576 was used as the *A. thaliana* promoter in this example.

Figure 3:
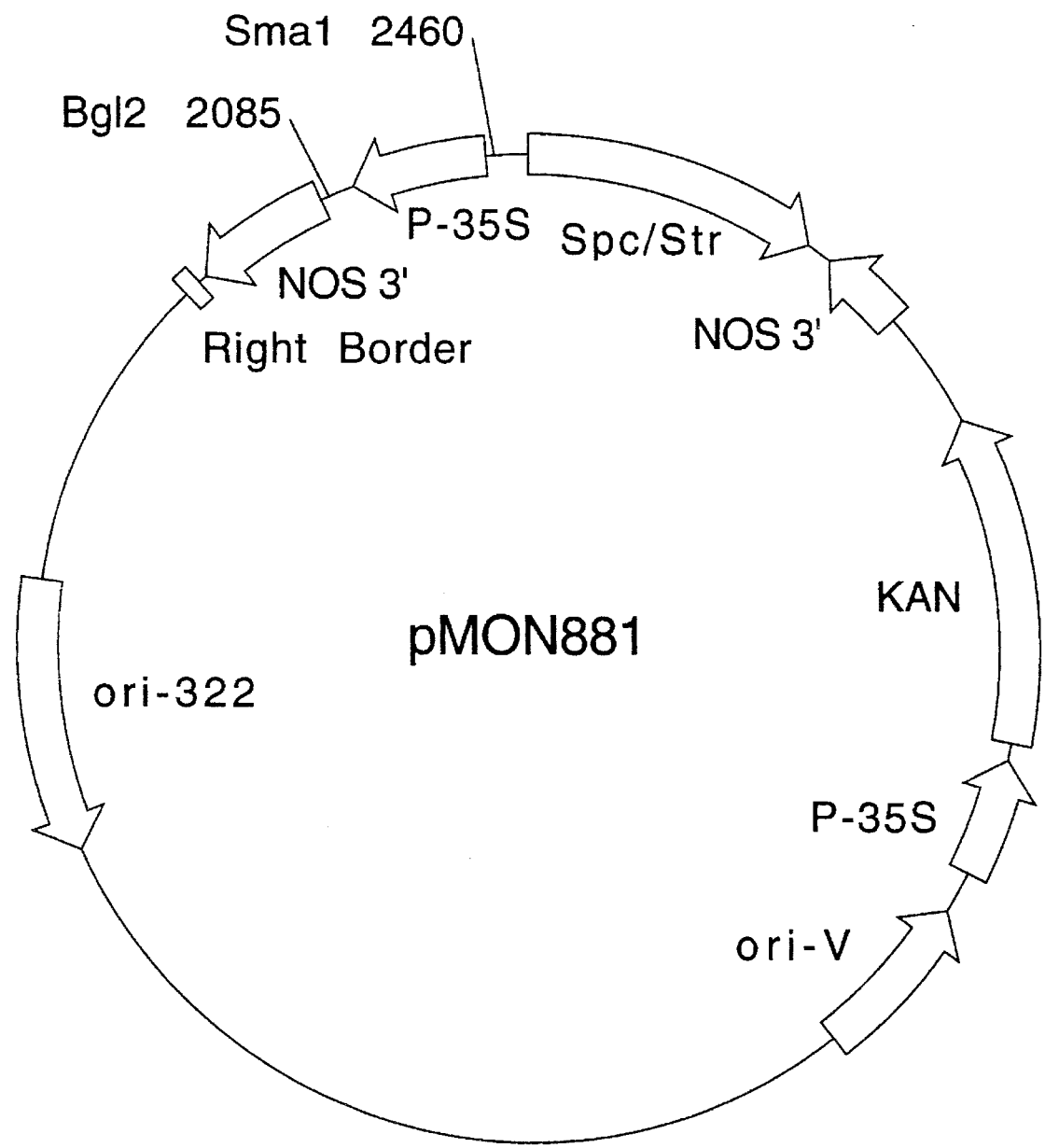
FIG. 3 shows a map of pMON881.

The plant transformation vector pMON881, as shown in FIG. 3, was used as the basis for making a construct to test the *A. thaliana* promoter in plants and is made up of the following segments of DNA. The first is a 0.93 kb fragment (AvaI to an engineered EcoRV site) isolated from transposon Tn7 that encodes bacterial spectinomycin/streptomycin resistance (Spc/Str), and is a determinant for selection in *E. coli* and *Agrobacterium tumefaciens*. This is joined to the 1.61 kb segment of DNA encoding a chimetic kanamycin resistance which permits selection of transformed plant cells. The chimetic gene (P-35S/KAN/NOS 3') consists of the cauliflower mosaic virus (CaMV) 35S promoter, the neomycin phosphotransferase type II (KAN) gene, and the 3' nontranslated region of the nopaline synthase gene (NOS 3') (Fraley et al. 1983). The next segment is the 0.75 kb ori-V containing the origin of replication from the RK2 plasmid. It is joined to the 3.1 kb SalI to PvuI segment of pBR322 (ori-322) which provides the origin of replication for maintenance in *E. coli* and the bom site for the conjugal transfer into the *A. tumefaciens* cells. The next segment is the 0.36 kb PvuI to BclI fragment from pTiT37 that carries the nopaline-type T-DNA right border (Fraley et al. 1985). The last segment is a 1.15 kb expression cassette consisting of the CaNIV 35S promoter, several unique restriction sites, and the NOS 3'.

Figure 4:
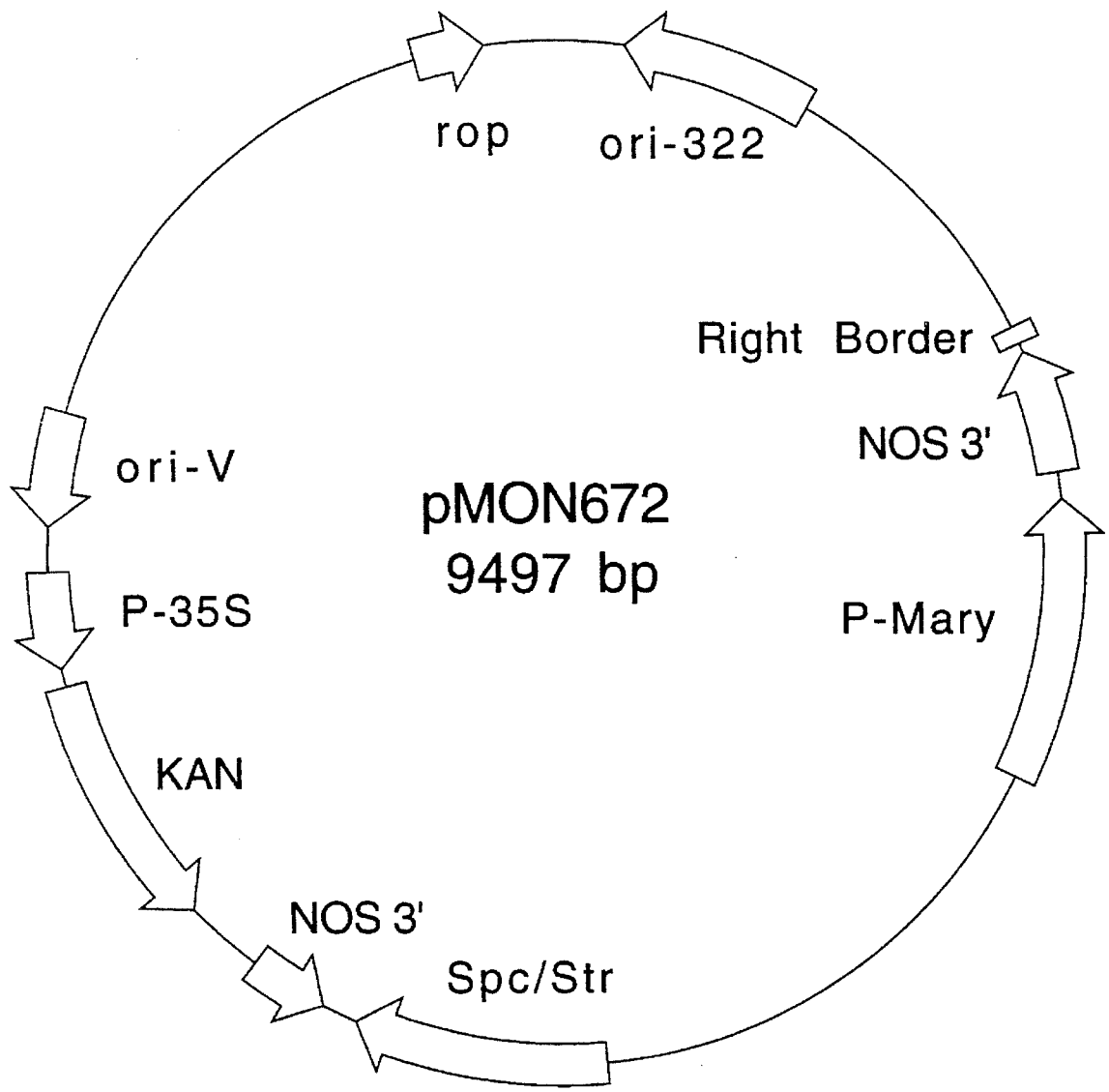
FIG. 4 shows a map of pMON672
Figure 5:
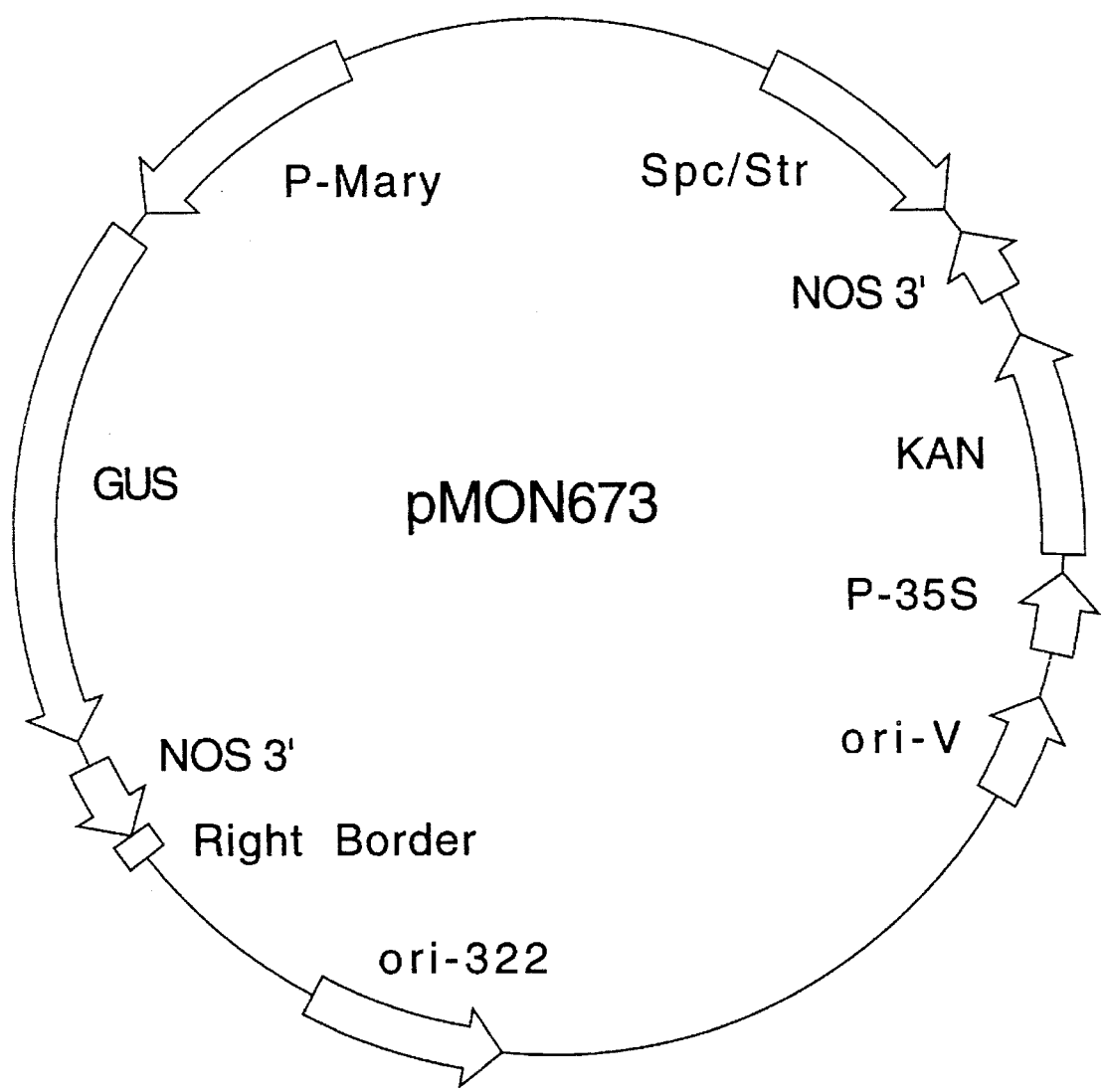
FIG. 5 shows a map of pMON673.

The CaMV35S promoter in the expression cassette of pMON881 was replaced by the *A. thaliana* promoter by inserting the 2.4 kb BglII-StuI fragment from pMON1576 into pMON881 digested with BglII and SmaI to create pMON672, a map of which is shown in FIG. 4. The coding sequence for B-glucuronidase (GUS) was then inserted as a 1.9 kb BamHI fragment into the BglII site of pMON672 to create pMON673, a map of which is shown in FIG. 5. The pMON673 vector contains a chimeric gene consisting of the *A. thaliana* promoter, GUS coding sequence, and NOS 3'.

The pMON673 vector was mobilized into *A. tumefaciens* strain ABI using the triparental conjugation system (Ditta et al. 1980). It was then transformed into *Nicotiana tabacum* and *Brassica napus* plants by the Agrobacterium mediated method of Horsch et al. (1985) and as adapted by Fry et al. (1986) for *Brassica napus* as previously described.

Transgenic plants containing pMON673 were assayed for GUS activity using the X-glue staining assay as described by Jefferson et al. (1987). Tissue containing active GUS stains blue in the presence of X-gluc. Histochemical staining showed that the engineered Arabidopsis promoter of the instant invention directed high levels of GUS expression in flower buds at a stage prior to meiosis and in the vegetative root and shoot apical meristem. The earliest floral buds which could be histologically detected were expressing the gene. Expression continued in these tissues through anthesis of the flower and continued in the developing embryo for some time following fertilization.

EXAMPLE 2

The *A. thaliana* promoter region as described in Example 1 was also tested for its ability to confer improved glyphosate tolerance through enhanced expression of tolerant EPSP synthase in tissues predicted to be more sensitive to glyphosate's deleterious effects. A chimeric gene consisting of the isolated *A. thaliana* promoter, variant genomic clones of the *A. thaliana* EPSP synthase coding region, and the 3' non-translated region of the pea ribulose bisphosphate carboxylase small subunit E9 gene (E9 3') (Coruzzi et al. 1984, and Morelli et al. 1985) was made for this purpose. First, an expression cassette containing the *A. thaliana* promoter, several unique restriction sites, and the E9 3' was made by inserting the 2.4 kb BglII-StuI fragment from pMON1576 into pMON921 digested with BglII and HincII to create pMON1581. A variant *A. thaliana* EPSP synthase coding region which contains two codon changes and encodes a glyphosate tolerant form of the enzyme from pMON982 was then inserted as a filled in ClaI-EcoRI fragment into the StuI site of the expression cassette of pMON1581 to create pMON989. This variant *A. thaliana* EPSP coding sequence is from a genomic clone and has a glycine to alanine substitution at position 101 and an aspartate for glycine substitution at position 144 of the mature protein. The isolation of this gene and its use is described in the co-pending, commonly assigned patent application entitled "Glyphosate-Tolerant 5-Enolpyruvyl-3-phosphoshikimate Synthases" filed on Jul. 17, 1989 and having Ser. No. 07/380,963 which is hereby incorporated by reference hereto.

Figure 6:
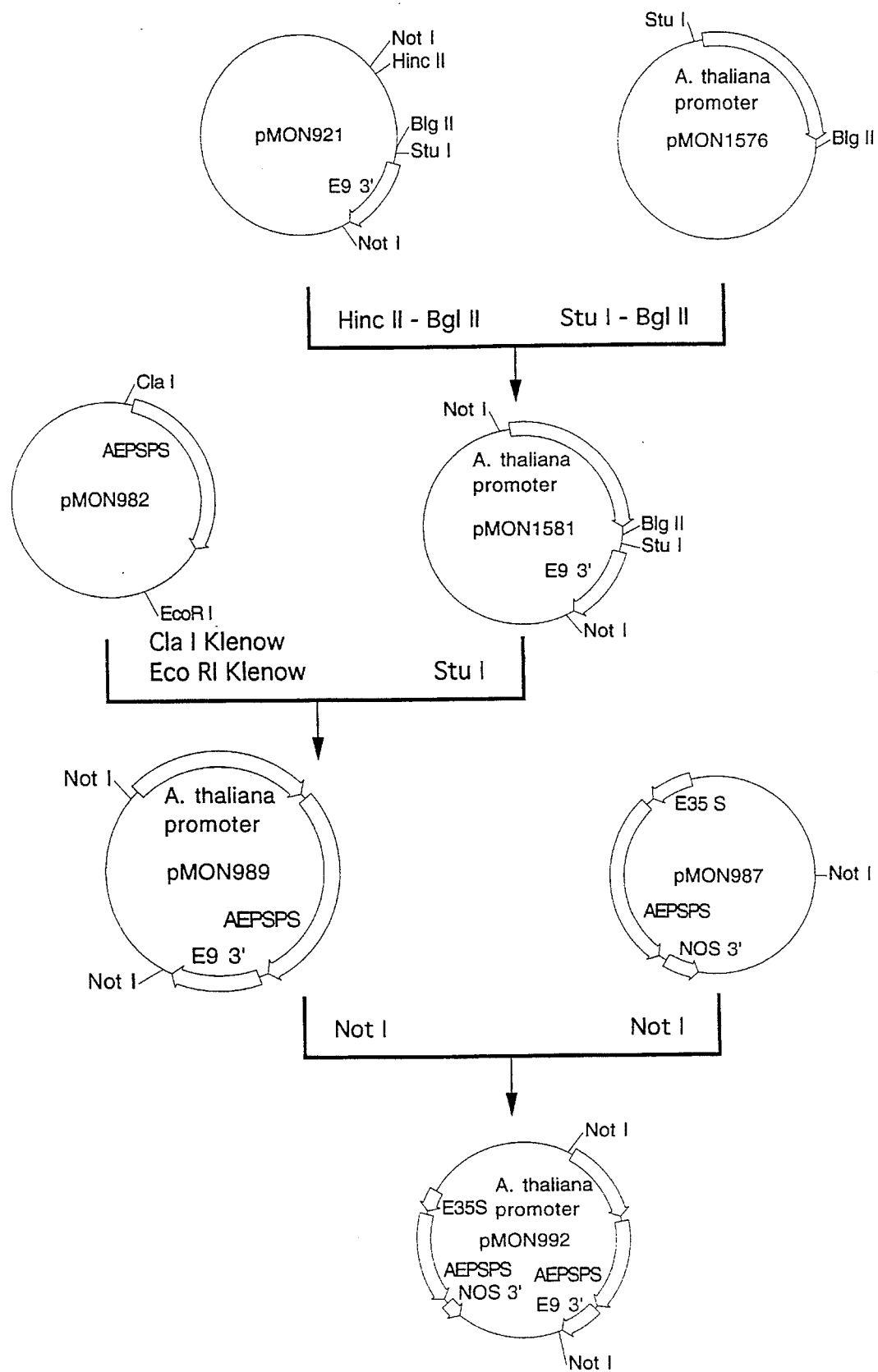
FIG. 6 shows a flow diagram illustrating the formation of pMON992.
Figure 7:
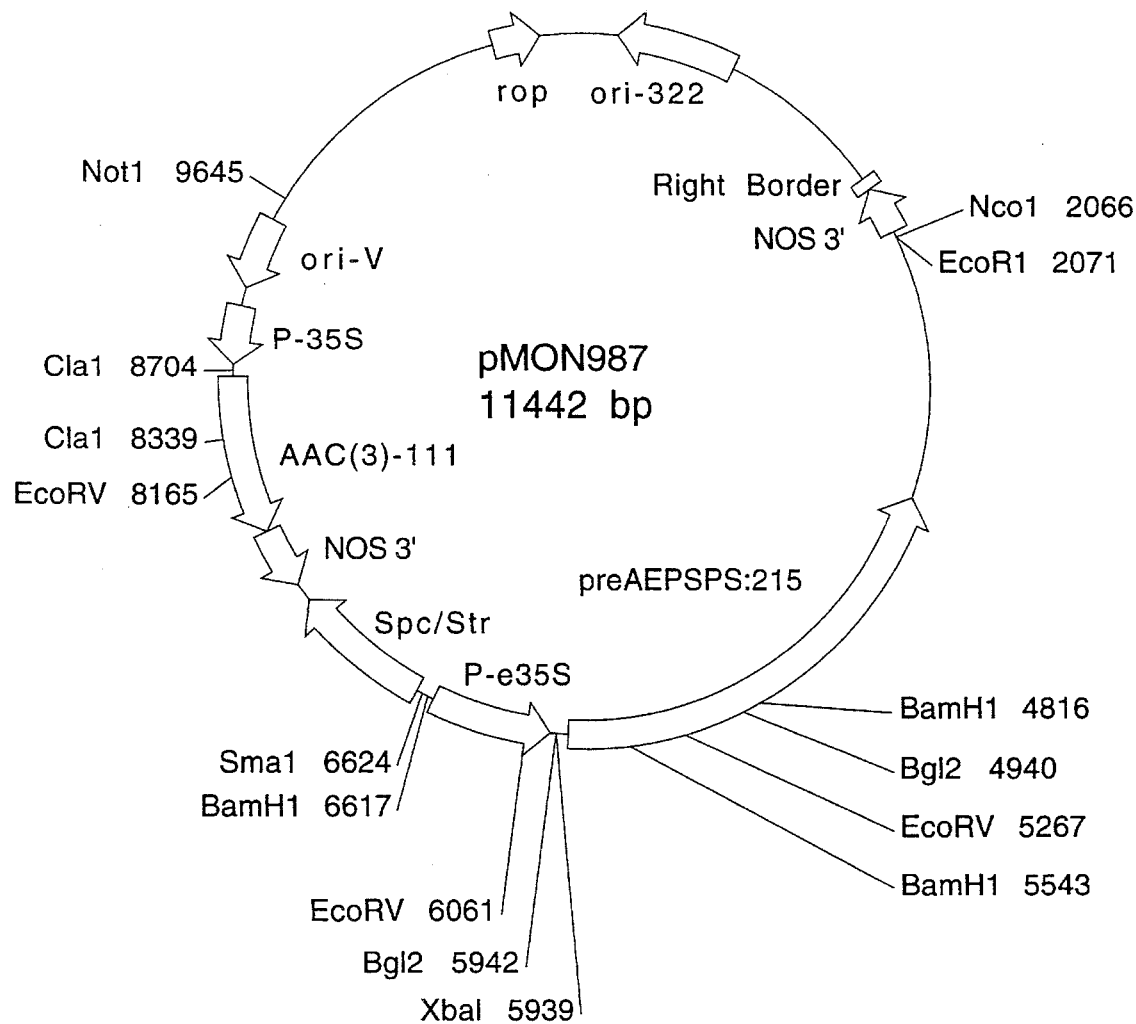
FIG. 7 shows a map of pMON987.
Figure 8:
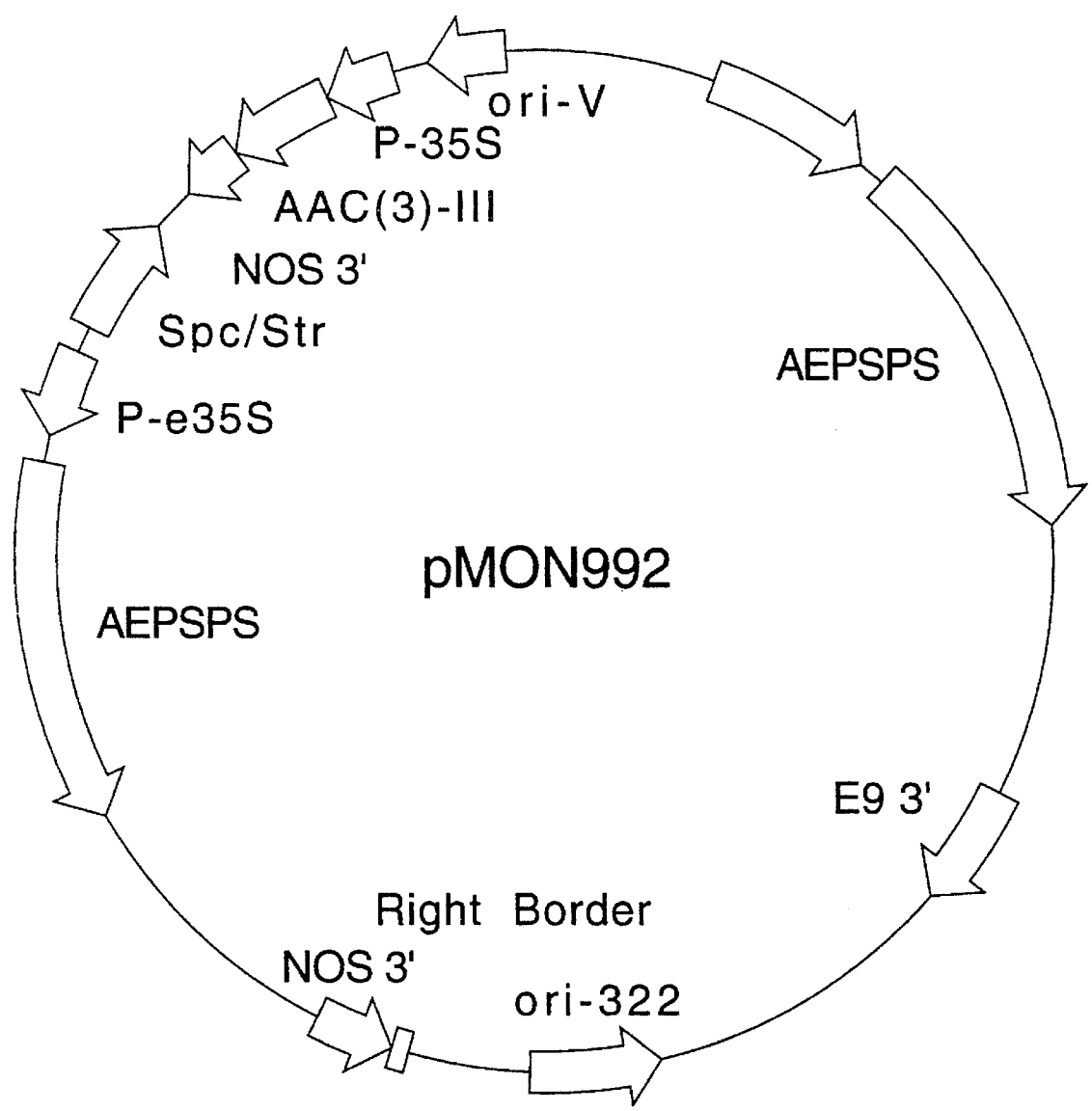
FIG. 8 shows a map of pMON992.

The chimeric gene from pMON989 was inserted as a NotI fragment into the NotI site of pMON987 to create pMON992. A flow diagram illustrating the construction of pMON992 is shown in FIG. 6. Plasmid maps of pMON987 and pMON992 are shown in FIG. 7 and FIG. 8, respectively. The pMON992 construct is made up of the following segments of DNA in addition to the chimeric gene from pMON989. The first is the 3.1 kb SalI to PvuI segment of pBR322 (Ori-322) which provides the origin of replication for maintenance in *E. coli* and the bom site for the conjugal transfer into the *A. tumefaciens* Cells. The next segment is the 0.36 kb PvuI to BclI fragment from pTiT37 that carries the nopaline-type T-DNA right border (Fraley et al. 1985). It is joined to a 4.7 kb chimeric gene consisting of the enhanced CaMV 35S promoter (Kay et al. 1987), a variant *A. thaliana* EPSP synthase coding region (the same as described for pMON989 above), and the NOS 3' polyadenylation signal. The next segment is a 0.93 kb fragment (AvaI to an engineered EcoRV site) isolated from transposon Tn7 that encodes bacterial spectinomycin/streptomycin resistance (Spc/Str), and is a determinant for selection in *E. coli* and *Agrobacterium tumefaciens*. This is joined to the 1.5 kb segment of DNA encoding a chimeric gentamicin resistance gene which permits selection of transformed plant cells. The chimeric gene (P-35S/AAC(3)-III/NOS3') consists of the CaMV 35S promoter, the gentamicin-3-N-acetyl-transferase type III gene (AAC(3)-III) (Hayford et al. 1988), and the NOS 3' polyadenylation signal. The last segment is the 0.75 kb ori-V containing the origin of replication from the RK2 plasmid.

Both pMON987 and pMON992 were mobilized into the *Agrobacterium tumefaciens* strain ACO using the triparental conjugation system (Ditta et al. 1980). Both were then transformed into *Nicotiana tabacura* and *Brassica napus* plants as previously described.

The transgenic, differentiated plants obtained containing the variant EPSP synthase gene as described above were analyzed for resistance to glyphosate. The transgenic plants containing the Arabidopsis EPSP synthase gene (as described) directed by the *Arabidopsis thaliana* promoter as also described above contained pMON992 while those plants containing the Arabidopsis EPSP synthase gene driven only by the enhanced CaMV35S promoter contained pMON987. These transgenic plants were planted and the seed from the R° plants harvested, threshed and dried before planting for a glyphosate spray test. The progeny were planted in 4-inch square pots of Metro 350 and three types of slow release fertilizers. A goal of twenty seedlings from each R° plant is desirable for testing. Germination frequency is usually high but overplanting ensures that twenty seedlings are present. The plants were thinned down by selecting the twenty most vigorous and erect seedlings seven to ten days after planting. A negative control (non-transformed, "Westar" variety) was planted at the same time to maintain quality and display the results. The plants were maintained and grown in a greenhouse environment. A sixteen-hour photoperiod and a temperature of 21° C. (day) and 15° C. (night) was maintained. Water soluble Peters Pete Lite fertilizer with an analysis of 20-19-18 was applied once per week or as needed.

Two plants from each R° progeny were not sprayed and served as controls to compare and measure the glyphosate tolerance. When the remaining plants reached the six to eight leaf stage, usually 20 to 28 days after planting, glyphosate was applied at a rate equivalent to 0.28 Kg/ha. Low rate technology using low volumes has been adopted. A volume of ten imperial gallons for 0.28 Kg/ha of glyphosate is standard in field tests. A laboratory test sprayer had been calibrated to deliver a consistent rate equivalent to field conditions.

Figure 9:
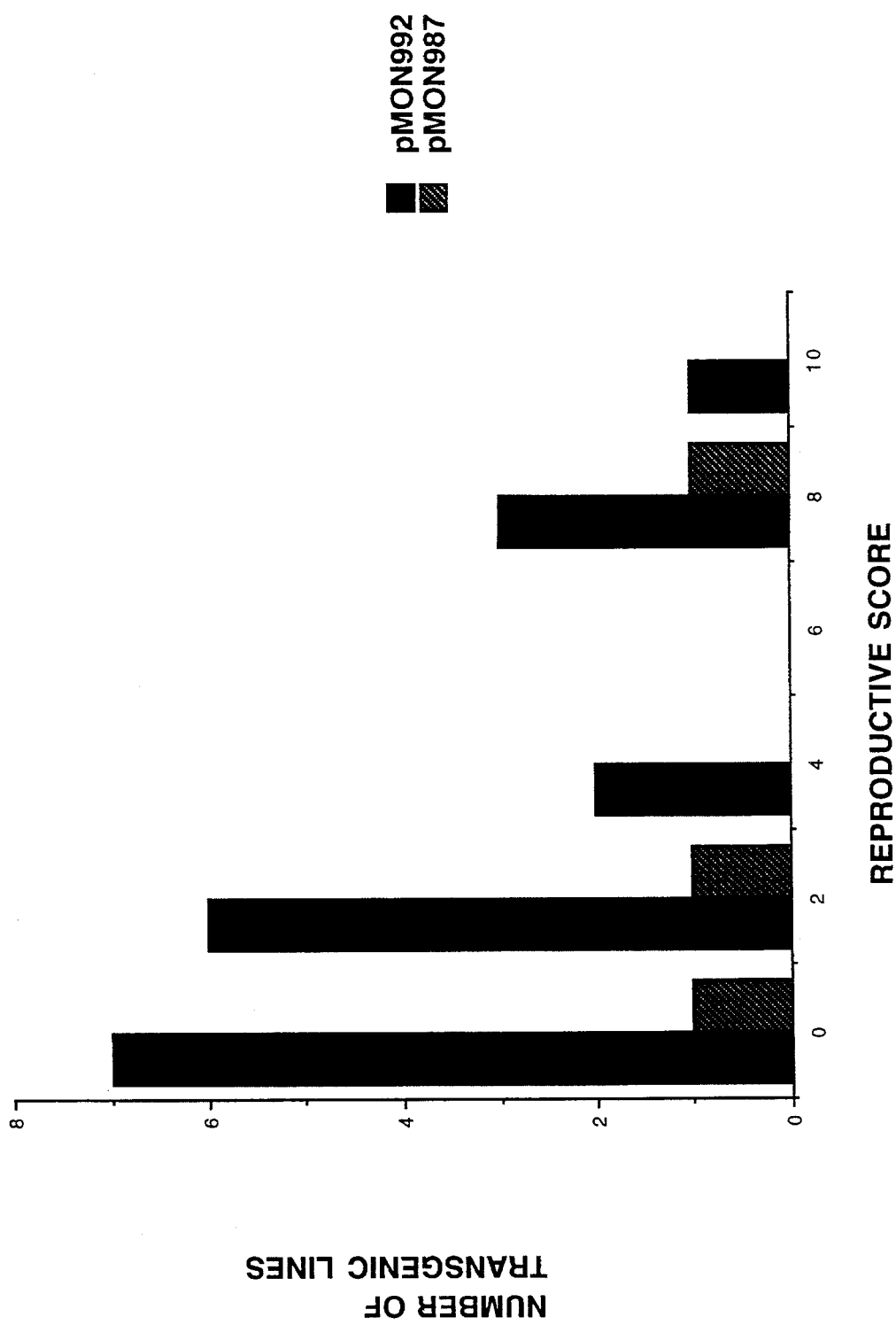
FIG. 9 shows the reproductive scores after glyphosate application of transgenic plants containing a variant EPSP synthase gene under the control of an *Arabidopsis thaliana* promoter region that confers high expression in meristematic tissue or an EPSP synthase gene only under the control of the enhanced CaMV35S promoter.

Results of reproductive evaluations are shown in FIG. 9. These calculations are based upon a numerical scoring system relative to nonsprayed controls. Reproductive scores are examined at 28 days after spraying and are based upon six distinct conditions in which the main meristein or flowers reacted to the glyphosate. The scale used is:

0=no floral bud development

2=floral buds, but aborted prior to opening

4=flowers without anthers, anthers should protrude past petals

6=flowers with normal appearing anthers, but sterile

8=flowers with partially sterile anthers

10=fully fertile flowers

FIG. 9 compares the reproductive scores of the total number of transgenic canola lines containing the meristematic promoter from *Arabidopsis thaliana* with three transgenic lines containing only the enhanced CaMV35S promoter. As is shown in FIG. 9, the plants transformed with the promoter of the present invention exhibit increased expression of resistant enzyme in the vegetative meristematic region of the plant by having higher reproductive scores in glyphosate spray tests than those of plants containing only the enhanced CaMV35S promoter. The transgenic lines that show reproductive scores of 0 or 2 are believed to be "escapes" where the chimeric gene is not being expressed, possibly as a result of incomplete transformation.

These results demonstrate an improved tolerance to glyphosate through expression of the genomic clone of the variant *Arabidopsis thaliana* EPSP synthase directed by the *A. thaliana* meristematic promoter.

EXAMPLE 3

Using a cDNA probe obtained from the *Arabidopsis thaliana* coding sequence of FIG. 1. this probe was used to screen genomic DNA libraries for homologous coding sequences that are highly expressed in meristematic tissue. The genomic libraries screened were from soybean, tomato, tobacco and canola. The hybridization methods previously described were utilized to determine if a coding sequence homologous to the cDNA probe of the *A. thaliana* coding sequence of FIG. 1 was present in the genome of the plant species chosen. The existence of a coding sequence homologous to the *Arabidopsis thaliana* coding sequence that is highly expressed in meristematic tissue was confirmed in each of the plant species tested; soybean, tomato, tobacco and canola. Once the homologous coding sequence is identified, the promoter region can be identified and isolated as described.

References

Bevan, M., et al., *Nature,* 304:.184 (1983).

Coruzzi, G., Broglie, R., Edwards, C., Chua, N.H., *EMBO J.,* 3: 1671 (1984).

Ditta, G., et al., *Proc. Natl. Acad. Sci. USA,* 77:7347–7351 (1980).

Feinberg, A., et al. *Anal. Biochem.,* 132:6 (1983).

Feinberg, A. and Vogelstein, B., *Anal. Biochem.* 137:266 (1984).

Fraley, R. T., Rogers, S. G., Horsch, R. B., Eichholtz, D. A., Flick, J. S., Fink, C. L., Hoffmann, N. L. and Sanders, P. R., *Bio/Technology,* 3:629–635 (1985).

Fraley, R. T., et al., *Proc. Natl. Acad. Sci. USA,* 80:4803 (1983).

Fry, J., Barnason, A. and Horsch, R., *Plant Cell Reports,* 6:321–325 (1987).

Gasser, C. S., Winter, J. A., Hironaka, C. M. and Shah, D. M., *J. of Biol. Chem.* 263:4280–4289 (1988).

Gasser, C. S., Budelier, K. A., Smith, A. G., Shah, D. M. and Fraley, R. T., Plant Cell, 1:15–24 (1989).

Hayford, M., et al., *Plant Physiol.,* 86:1216–1222 (1988).

Herrera-Estrella, L., et al., *Nature,* 303:209 (1983).

Horsch R. and Jones G., *In Vitro,* 16:103–108 (1980).

Horsch R., Fry J., Hoffman, N., Wallworth, M., Eicholtz, D., Rogers, S., Fraley, R., *Science,* 227:1229–1231 (1985).

Jefferson, R. A., Kavanagh, T. A. and Bevan, M. W., *EMBO J.,* 6: 3901–3907 (1987).

Kay, R., Chan, A., Daly, M., McPherson, J., *Science,* 236:1299–1302 (1987).

Klee, H., et al., *Bio/Technology,* 3:637 (1985).

Maniatis, T., Fritsch, E. F. and Sambrook, *Molecular Cloning,* pp. 320–322, Cold Spring Harbor Laboratory (1982).

Morelli, G., Nagy, F., Fraley, R. T., Rogers, S. G., Chua, N. H., *Nature,* Vol. 315, pp. 200–204 (1985).

Rochester, D. E., Winter, J. A. and Shah, D. M., *EMBO J.,* 5: 451–458 (1986).

Sanger, F., et al., *Proc. Natl. Acad. Sci. USA,* 74:5463–5467 (1977).

Stringam, G. R., *Plant Science Letters,* 9:115–119 (1977)

Young, R. A. and Davis, R. W., *Proc. Natl. Acad. Sci. USA,* 80: 1194–1198 (1983).

We claim:

1. An isolated DNA molecule consisting essentially of a plant promoter region from *Arabidopsis thaliana* located upstream to a structural DNA sequence which hybridizes to a cDNA probe derived from the structural DNA sequence shown in FIG. 1, said plant promoter region, when operably linked to a heterologous gene, causes transcription in meristematic tissue or regions of rapidly dividing plant cells.

2. A plant promoter region of claim 1 wherein said promoter region is about 2.4 kb in length.

3. A DNA molecule which comprises:

(a) a plant promoter region from *Arabidopsis thaliana* which causes transcription in meristematic tissue or regions of rapidly dividing plant cells, said promoter region naturally located upstream to a structural DNA sequence which hybridizes to a cDNA probe derived from the structural DNA sequence shown in FIG. 1; operably linked to (b) a heterologous structural gene; operably linked to (c) a 3' non-translated DNA sequence which functions in plant cells to cause the addition of polyadenylated ribonucleotides to the 3' end of the transcribed mRNA sequence.

4. A DNA molecule of claim 3 wherein said plant promoter region is about 2.4 kb in length.

5. A DNA molecule of claim 3 wherein said heterologous structural gene of part (b) encodes a fusion polypeptide of a chloroplast transit peptide and 5-enolpyruvylshikimate-3-phosphate synthase, which chloroplast transit peptide permits the 5-enolpyruvylshikimate-3-phosphate synthase to be imported into a chloroplast of a plant cell.

6. A transformed plant cell which contains a DNA molecule which comprises:

(a) a plant promoter region from *Arabidopsis thaliana* which causes transcription in meristematic tissue or regions of rapidly dividing plant cells, said promoter region naturally located upstream to a structural DNA sequence which hybridizes to a cDNA probe derived from the structural DNA sequence shown in FIG. 1; operably linked to (b) a heterologous structural gene; operably linked to (c) a 3' non-translated DNA sequence which functions in plant cells to cause the addition of polyadenylated ribonucleotides to the 3' end of the transcribed mRNA sequence.

7. A transformed plant cell of claim 6 wherein said plant promoter region is about 2.4 kb in length.

8. A transformed plant cell of claim 6 wherein said heterologous structural gene encodes a fusion polypeptide of a chloroplast transit peptide and 5-enolpyruvylshikimate-3-phosphate synthase, which chloroplast transit peptide permits the 5-enolpyruvylshikimate-3-phosphate synthase to be imported into a chloroplast of a plant cell.

9. A transformed plant cell of claim 8 wherein said chloroplast transit peptide is from a plant EPSPS gene.

10. A differentiated plant consisting of plant cells which contain a DNA molecule which comprises:

(a) a plant promoter region from *Arabidopsis thaliana* which causes transcription in meristematic tissue or regions of rapidly dividing plant cells, said promoter region naturally located upstream to a structural DNA sequence which hybridizes to a cDNA probe derived from the structural DNA sequence shown in FIG. 1, which is operably linked to;

(b) a heterologous stuctural gene, which is operably linked (c) a 3' non-translated DNA sequence which functions in plant cells to cause the addition of polyadenylated ribonucleotides to the 3' end of the transcribed mRNA sequence.

11. A plant of claim 10 wherein said plant promoter region is about 2.4 kb in length.

12. A plant of claim 10 selected from the group consisting of, tomato, potato, tobacco, lettuce, sunflower, offseed rape, flax, cotton, sugarbeet, celery, soybean, alfalfa, cucumber, carrot and cauliflower.

13. A plant of claim 12 wherein said structural gene of part (b) encodes a fusion polypspride of a ehloroplast transit peptide and 5-enolpyruvylshikimate-3-phosphate synthase, which chloroplast transit peptide permits the 5-enolpyruvylshikimate-3-phosphate synthase to be imported into a chloroplast of a plant cell.

14. A plant of claim 13 wherein said chloroplast transit peptide is from a plant EPSPS gene.

15. A seed from a plant of claim 10.

16. A seed from a plant of claim 12.

17. A seed from a plant of claim 14.

* * * * *